United States Patent [19]
Buckle et al.

[11] 4,211,791
[45] Jul. 8, 1980

[54] INDANEDIONES

[75] Inventors: Derek R. Buckle, Redhill; Harry Smith, Maplehurst, near Horsham, both of England

[73] Assignee: Beecham Group Limited, England

[21] Appl. No.: 963,965

[22] Filed: Nov. 27, 1978

Related U.S. Application Data

[60] Division of Ser. No. 780,246, Mar. 22, 1978, Pat. No. 4,136,192, which is a continuation-in-part of Ser. No. 722,868, Sep. 13, 1976, abandoned.

[30] Foreign Application Priority Data

| Sep. 23, 1975 | [GB] | United Kingdom | 39041/75 |
| Sep. 23, 1975 | [GB] | United Kingdom | 39042/75 |
| Feb. 4, 1976 | [GB] | United Kingdom | 4321/76 |
| Jun. 12, 1976 | [GB] | United Kingdom | 24450/76 |
| May 22, 1976 | [GB] | United Kingdom | 21276/76 |
| May 22, 1976 | [GB] | United Kingdom | 21277/76 |
| Feb. 11, 1977 | [GB] | United Kingdom | 5833/77 |
| Feb. 11, 1977 | [GB] | United Kingdom | 5840/77 |
| Feb. 11, 1977 | [GB] | United Kingdom | 5856/77 |

[51] Int. Cl.$^2$ .............. C07C 79/36; C07C 121/52; A61K 31/275; A61K 31/12

[52] U.S. Cl. .................. 424/304; 424/309; 424/317; 424/324; 424/331; 260/465 D; 260/465 E; 260/465 F; 260/562 P; 260/574; 260/575; 560/21; 560/139; 562/435; 568/306

[58] Field of Search ........ 260/465 D, 465 F, 590 FA, 260/559 R, 574, 575, 562 P; 266/465 E, 465 F; 424/304, 331, 309, 317, 324; 560/21, 139; 562/435

[56] References Cited

U.S. PATENT DOCUMENTS

| 3,925,557 | 12/1975 | Buckle et al. | 260/590 FA |
| 4,012,407 | 3/1977 | Doyle et al. | 260/465 F |

Primary Examiner—Natalie Trousof
Assistant Examiner—Jane T. Fan
Attorney, Agent, or Firm—Jacobs & Jacobs

[57] ABSTRACT

Bicyclic compounds useful in the prophylaxis and treatment of allergic diseases, pharmaceutical compositions containing the same, methods of administration of the compositions, intermediates useful in preparing the compounds and conversion of the intermediates to the bicyclic compounds. Examples of compounds are substituted coumarins and indanediones and their pharmaceutically acceptable salts.

98 Claims, No Drawings

INDANEDIONES

This is a divisional of our copending application Ser. No. 780,246, filed 3/22/78 now U.S. Pat. No. 4,136,192, issued 1/23/77 which is a continuation-in-part of U.S. Ser. No. 722,868, filed 9/13/76, now abandoned.

This invention relates to bicyclic compounds which are useful in the prophylaxis and treatment of allergic diseases.

It is known that some types of cells are activated by antibody-antigen combinations and release substances which mediate allergic response. It has been reported that SRS-A (the slow reacting substance of anaphylaxis) released from such cells which have been activated by antibody-antigen combinations plays an important role in the development of allergic and asthmatic phenomena.

In U.S. Pat. Nos. 3,936,504, 3,925,557, 3,988,476, 3,978,231, 3,974,289 and U.S. patent application Ser. No. 572,226 we have disclosed bicyclic cyano and nitro compounds which have useful activity in that they inhibit the release of mediator substances from cells which have been activated by the type of antibody-antigen combination described above. We have now discovered that compounds of formula (I) below have useful activity in mammals in that they not only protect against the antibody antigen release of SRS-A and other mediators of the allergic response but also they inhibit the action of SRS-A. These compounds are therefore useful in the prophylaxis and treatment of diseases in which allergic mediator substances control the symptoms, for example bronchial asthma, rhinitis, hay fever, allergic eczema, etc.

Accordingly, this invention provides a compound of formula (I) and pharmaceutically acceptable salts thereof:

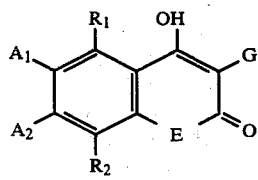

wherein one of $A_1$ or $A_2$ is a group of formula (II):

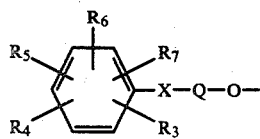

and $R_1$, $R_2$ and the one of $A_1$ or $A_2$ not representing group of formula (II) are the same or different and represent hydrogen, lower alkyl, lower alkoxy, lower alkenyl, lower alkynyl or, the one of $A_1$ or $A_2$ which does not represent a group of formula (II) taken together with one of $R_1$ or $R_2$ to which it is adjacent represents a 1,4-buta-1,3-dienylene group or an alkylene group containing from 3 to 5 carbon atoms inclusive provided that at least one of $R_1$, $R_2$, $A_1$ and $A_2$ is hydrogen; E represents oxygen or a covalent bond, G represents nitro or cyano; X is oxygen or a methylene group and Q represents a linear alkylene group containing from 1 to 7 carbon atoms inclusive, one methylene group within the group Q, other than a methylene covalently bound to an ether oxygen, being optionally substituted with hydroxyl and $R_3$, $R_4$, $R_5$, $R_6$ and $R_7$ each representing hydrogen, halogen, nitro, hydroxy, cyano, carboxyl, amino, lower alkyl, lower alkenyl, lower alkynyl, lower alkoxy, lower alkoxy carbonyl, lower acyl, lower acyloxy, mono- and di-lower alkyl amino, mono- and di-lower acylamino, phenyl, lower alkylphenyl, phenoxycarbonyl, benzyloxycarbonyl, or any two of $R_3$ to $R_7$ when on adjacent carbon atoms together represent an alkylene group containing from 3 to 5 carbon atoms inclusive, or a 1,4-buta-1,3-dienylene group.

When used herein the terms lower alkyl lower alkenyl and lower alkynyl lower alkoxy and lower acyl mean such groups containing from 1 to 6 carbon atoms inclusive.

The compounds of formula (I) may exist in a number of tautomeric forms, and it is to be understood that whenever in the specification we refer to compounds of the formula (I) we mean to include tautomeric forms thereof. The tautomeric forms predominant for a particular compound of formula (I) are dependent on the nature of the substituent.

When E represents a bond, the predominant tautomers include:

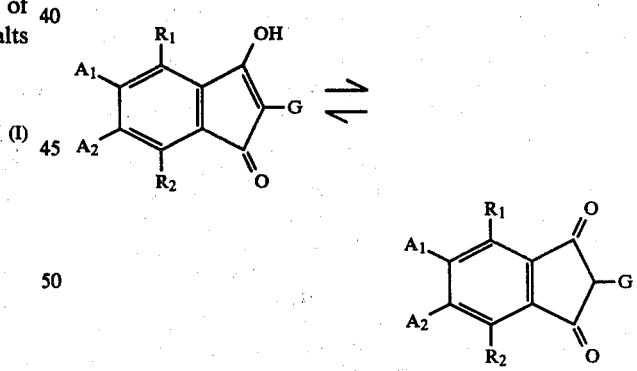

When E represents an oxygen atom, the predominant tautomers include:

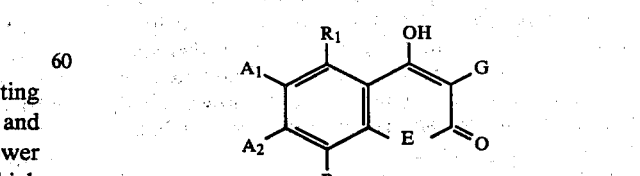

Compounds of formula (I) where G is nitro also may exist in the following additional tautomeric forms:

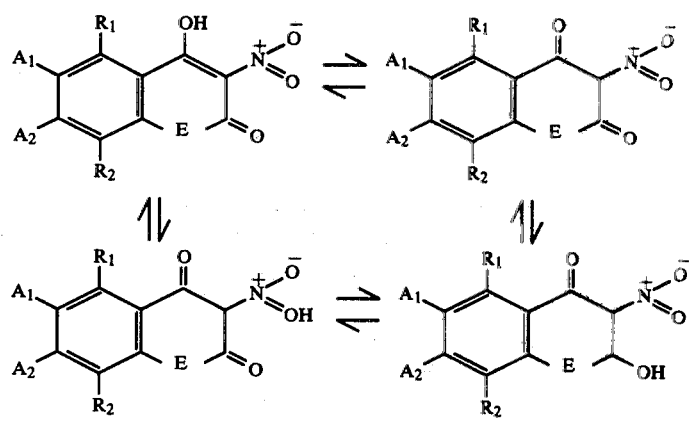

Examples of suitable lower alkyl substituents falling within the definitions of $R_1$ to $R_7$ are methyl, ethyl, n- and iso-propyl, n-, iso and t-butyl.

Examples of suitable lower alkenyl groups represented by one of $A_1$ or $A_2$ and $R_1$ to $R_7$ are 2-propenyl; 2- and 3-butenyl; 2-, 3- and 4-pentenyl; 2-, 3-, 4- and 5-hexenyl; 1-, and 2-methyl-2-propenyl; 1-, 2-, and 3-methyl-2- and 3-butenyl; 1-, 2-, 3-, and 4-methyl-2, 3-, and 4-pentenyl; 1-, and 2-ethyl-1-propenyl; 1-, 2- and 3-ethyl-2- and 3- butenyl.

Examples of suitable lower alkynyl groups represented by one of $A_1$ or $A_2$ and $R_1$ to $R_7$ are 2-propynyl; 2- and 3- butynyl; 2-, 3- and 4-pentynyl; 2-, 3-, 4- and 5-hexynyl; 1-, and 2- methyl-2-propynyl; 1-, 2-, and 3-methyl-2- and 3-butynyl; 1-, 2-, 3- and 4-methyl-2-, 3-, and 4- pentynyl; 1-, and 2- ethyl-2-propynyl; 1-, 2-, and 3-ethyl-2- and 3-butynyl.

Examples of suitable lower alkoxy substituents falling within the definitions of one of $A_1$ or $A_2$ and $R_1$ to $R_7$ are methoxy, ethoxy, n- and iso- propoxy, n, iso- and t-butoxy.

Examples of suitable lower acyl groups included within the definition of $R_3$ to $R_7$ are acetyl, propionyl, n- and iso-butyryl. Examples of lower alkoxy carbonyl substituents included within the definition of $R_3$ to $R_7$ are methoxycarbonyl, ethoxycarbonyl, n- and iso-propoxycarbonyl, n- and iso-butoxycarbonyl. Examples of lower acyloxy groups falling within the definition of $R_3$ to $R_7$ are acetoxy, propionoxy, butyryloxy, and pentanoyloxy. These previously mentioned examples of lower alkyl and lower acyl groups are also suitable as examples of the lower alkyl, and lower acyl groups contained in the mono- and di-lower alkyl and lower acyl amino substituents included within the definition of $R_3$ to $R_7$. The suitable halogen atoms included within the definition of $R_3$ to $R_7$ are fluorine, chlorine and bromine. The most suitable halogen is fluorine.

The alkyl, alkoxy, alkenyl, alkynyl, acyl, acyloxy, and alkoxy carbonyl groups represented by one of $A_1$ or $A_2$ and $R_1$ to $R_7$ are suitably unbranched. Where a highly substituted compound of formula (I) is required it will be appreciated that the substituents are to be chosen for steric compatability. For example where two or three of the substituents are groups of complex stereochemistry, such as highly branched lower alkyl, lower alkoxy or similar groups, then these will not occupy adjacent positions.

Examples of linear alkylene groups represented by Q are methylene, ethylene, propylene, butylene, pentylene, hexylene or heptylene. The optional hydroxyl group may occupy any position on any such alkylene groups other than methylene bonded to an ether oxygen. Generally the optional hydroxy substituent enhances water solubility. It is appreciated in this regard that when a methylene within the group Q is substituted with hydroxyl, then the methylene so substituted is asymmetric. It is therefore to be understood that when the compounds of this invention are referred to herein then mixtures of enantiomers as well as pure enantiomers are included. Suitably at least one of $R_3$ to $R_7$ represents hydrogen, and more suitably two of $R_3$ to $R_7$ are hydrogen. The remaining substituents are all different.

Within the general scope of the compounds of this invention there are certain more suitable subgroups of compounds, depending upon the nature of the substituents $A_1$, $A_2$ and $R_1$ to $R_7$. Thus a first more suitable subgroup consists of the comounds of formula (I) wherein $R_1$, $R_2$ and one of $A_1$ or $A_2$ which is not a group of formula (II) represent hydrogen or lower alkyl, the other one of $A_1$ or $A_2$ and $R_3$ to $R_7$ are as previously defined. More suitably $R_2$ is lower alkyl, and $R_1$ and one of $A_1$ or $A_2$ are both hydrogen.

A second more suitable group of compounds falling within the general scope of this invention are those in which the phenyl ring of the substituent of formula (II) bears no more than two polar groups.

This class of compound is of the formula (I) and $R_1$, $R_2$, $A_1$ and $A_2$ are as previously defined and $R_3$ is hydrogen, lower alkyl, lower alkoxy, lower acyl, lower acyloxy, lower alkoxycarbonyl, phenyl cyano, carboxy, halogen, nitro, hydroxy, amino, mono- and di-lower alkylamino, mono and di lower acylamino, $R_4$ is hydrogen, lower alkyl, lower alkoxy, lower acyl, lower acyloxy or lower alkoxycarbonyl and $R_5$ is hydrogen or a lower alkyl group; and in addition any two of $R_3$, $R_4$ and $R_5$ when on adjacent carbon atoms represent an alkylene group containing from 3 to 5 carbon atoms inclusive or a 1,4-but-1,3-dienylene group, and $R_6$ and $R_7$ are both hydrogen.

A third suitable group of compounds falling within the scope of this invention are those in which the phenyl ring of the substituent (II) bears a single lower alkyl substituent i.e. $R_3$ is lower alkyl and $R_4$ to $R_7$ are all hydrogen. Particularly suitable lower alkyl groups are methyl, ethyl and n-propyl. Most advantageously this lower alkyl group occupies position 2' of the phenyl ring.

A fourth suitable group of compounds falling within the scope of this invention are those in which the phenyl ring of substituent (II) bears a single fluorine atom, i.e. $R_3$ is fluorine and $R_4$ to $R_7$ are all hydrogen. Most suitably the fluorine substituent occupies position 4' of the phenyl ring.

A fifth group of compounds falling within the scope of this invention are those in which $R_3$ is a fluorine atom at position 4' of the phenyl ring of substituent (II)

$R_4$ is a lower alkyl group most suitably propyl, at position 2', and $R_5$ to $R_7$ are all hydrogen atoms.

A particularly suitable combination of groups for inclusion in the phenyl ring of the substituent (II) and which confer a favourable level of activity consists of one polar group, one hydrophilic group e.g. $R_4$ is hydroxyl and one hydrophobic group e.g. $R_5$ is lower alkyl, $R_6$ and $R_7$ are both hydrogen. It is particularly suitable in such a combination that the hydroxyl group $R_3$ occupies position 3', the lower acyl group $R_4$ occupies position 4', and the lower alkyl group $R_5$ occupies position 2' of the phenyl ring. In this combination $R_4$ is most suitably acetyl and $R_5$ is most suitably n-propyl.

The positions referred to by number in the phenyl ring of substituent (II) are as indicated below:

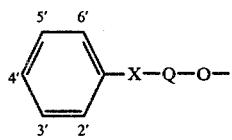

A further suitable group of compounds falling within the scope of this invention, bear no substituents in the phenyl ring of substituent (II) and are of the general formula (I), wherein one of $A_1$ or $A_2$ is a substituent of formula (II), in which $R_3$ to $R_7$ are all hydrogen, and $R_1$ and $R_2$ and the one of $A_1$ or $A_2$ which is not a substituent of formula (II) are all hydrogen.

Within this last mentioned group of compounds, those compounds of the general formula (I), wherein $R_1$ and $R_2$ also represent hydrogen, are preferred for their ease of synthesis. Preferably $A_2$ represents a substituent of formula (II).

Within the general scope of compounds falling within the scope of this invention, G may be nitro or cyano and E may be a bond or oxygen. Compounds of formula (I) where G is nitro have a more favourable level of activity than those wherein G is cyano. Those compounds of formula (I) in which E is a bond have in general a more favourable level of activity as compared with compounds in which E is oxygen. Also within the general scope of the invention X may represent methylene or an oxygen atom. Where X is methylene the compounds where Q is also methylene have useful oral absorbtion properties. Where Q is ethylene, propylene, butylene or pentylene one methylene group may be optionally substituted with hydroxyl. Compounds where X is oxygen have in general a more favourable level of intrinsic anti-allergic activity. Where X is an oxygen atom Q is suitably methylene, but more suitably is ethylene. Similarly where Q is propylene, butylene, pentylene or hexylene one methylene may be optionally substituted by hydroxyl, a particularly suitable group being 2-hydroxy propylene.

Examples of specific compounds of formula (I) wherein G is nitro, E is oxygen and X is a methylene group, are:
4-hydroxy-3-nitro-6-(2-phenylethoxy) coumarin,
4-hydroxy-3-nitro-7-(2-phenylethoxy) coumarin,
4-hydroxy-3-nitro-7-(3-phenylpropoxy) coumarin, and
4-hydroxy-3-nitro-7-(4-phenylbutoxy) coumarin.
7-(2-[4-fluorophenyl]ethoxy)-4-hydroxy-3-nitrocoumarin
7-(3-[4-acetylphenyl]propoxy)-4-hydroxy-3-nitrocoumarin
7-(4-[4-chlorophenyl]butoxy)-4-hydroxy-3-nitrocoumarin
4-hydroxy-7-(4-[4-methylphenyl]butoxy)-3-nitrocoumarin
7-(2-[2-n-propyl-4-fluorophenyl]-ethoxy)-4-hydroxy-3-nitrocoumarin
Of these compounds;
4-hydroxy-3-nitro-7-(2-phenyl ethoxy) coumarin and
7-(2-[2-n-propyl-4-fluorophenyl]-ethoxy)-4-hydroxy-3-nitrocoumarin are particularly preferred.

Examples of compounds of formula (I) wherein G is nitro, E is oxygen and X is oxygen are;
4-hydroxy-3-nitro-6-(3-phenoxypropoxy) coumarin
4-hydroxy-3-nitro-6-(2-phenoxyethoxy) coumarin
4-hydroxy-3-nitro-6-(6-phenoxyhexoxy) coumarin
4-hydroxy-3-nitro-7-(3-phenoxypropoxy) coumarin
4-hydroxy-3-nitro-7-(5-phenoxypentoxy) coumarin
4-hydroxy-3-nitro-7-(4-phenoxybutoxy) coumarin
4-hydroxy-3-nitro-7-(2-hydroxy-3-phenoxypropoxy) coumarin
4-hydroxy-3-nitro-7-(6-phenoxyhexoxy) coumarin and
4-hydroxy-3-nitro-7-(2-phenoxyethoxy) coumarin
7-(4-chlorophenoxymethoxy)-4-hydroxy-3-nitrocoumarin
7-(2-[4-acetyl-3-hydroxy-2-n-propylphenoxy]ethoxy)-4-hydroxy-3-nitrocoumarin
4-Hydroxy-3-nitro-7-(3-phenoxypropoxy)-8-n-propyl-coumarin
7-(3-[4-Chlorophenoxy]propoxy)-4-hydroxy-3-nitrocoumarin
7-(3-[4-Carboxyphenoxy]propoxy)-4-hydroxy-3-nitrocoumarin
7-(3-[4-Carbomethoxyphenoxy]propoxy)-4-hydroxy-3-nitrocoumarin
7-(3-[4-Acetylphenoxy]propoxy)-4-hydroxy-3-nitrocoumarin
4-Hydroxy-7-(3-[4-methyl-2-nitrophenoxy]propoxy)-3-nitrocoumarin
7-(3-[4-Acetyl-3-hydroxyphenoxy]propoxy)-4-hydroxy-3-nitrocoumarin
4-Hydroxy-7-(3-[2-methylphenoxy]propoxy)-3-nitrocoumarin
7-(3-[4-Acetyl-3-hydroxy-2-n-propylphenoxy]propoxy)-4-hydroxy-3-nitrocoumarin
7-(3-[4-Carboxyphenoxy]-2-hydroxy-propoxy)-4-hydroxy-3-nitrocoumarin
4-Hydroxy-7-(2-hydroxy-3-phenoxypropoxy)-3-nitrocoumarin
7-(3-[4-Acetyl-2-n-propylphenoxy]-2-hydroxypropoxy)-4-hydroxy-3-nitrocoumarin
7-(3-[4-Acetyl-3-hydroxyphenoxy]2-hydroxypropoxy)-4-hydroxy-3-nitrocoumarin
7-(3-[4-Acetyl-3-hydroxy-2-methyl-phenoxy]-2-hydroxypropoxy-4-hydroxy-3-nitrocoumarin
7-(3-[4-Acetyl-2-ethyl-5-hydroxyphenoxy]-2-hydroxypropoxy)-4-hydroxy-3-nitrocoumarin
6-(3-[4-Acetyl-3-hydroxy-2-n-propyl-phenoxy]-2-hydroxypropoxy)-4-hydroxy-3-nitrocoumarin
4-Hydroxy-7-(2-hydroxy-3-[3-hydroxy-4-propionyl-2-n-propyl-phenoxy]propoxy)-3-nitrocoumarin
4-Hydroxy-7-(3-[3-methylphenoxy]propoxy)-3-nitrocoumarin 4-Hydroxy-7-(3-[4-methylphenoxy]propoxy)-3-nitrocoumarin 4-Hydroxy-7-(3-[4-methoxyphenoxy]propoxy)-3-nitrocoumarin 7-(3-[4-Fluorophenoxy]propoxy)-4-hydroxy-3-nitrocoumarin 7-(3-[4-Cyanophenoxy]propoxy)-4-hydroxy-3-nitrocoumarin 4-Hydroxy-7-(3-[4-phenylphenoxy]propoxy)-3-nitrocoumarin 4-Hydroxy-3-nitro-7-(3-[5,6,7,8-tetrahydro-2-naphthyloxy]propoxy) coumarin 4-Hydroxy-7-(2-hydroxy-3-[2-n-propyl-phenoxy]-propoxy)-3-nitrocoumarin 7-(3-[4-Acetyl-3-hydroxy-2-n-propylphenoxy]-2-hydroxypropoxy)-4-hydroxy-3-nitrocoumarin 4-Hydroxy-5-methyl-3-nitro-7-(3-phenoxypropoxy) coumarin 6-Ethyl-4-hydroxy-3-nitro-7-(3-phenoxy-propoxy) coumarin 7-(3-[4-Acetyl-3-hydroxy-2-n-propylphenoxy]-2-hydroxypropoxy)-4-hydroxy-8-methyl-3-nitrocoumarin 7-(3-[4-Acetyl-3-hydroxy-2-n-propylphenoxy]-2-hydroxypropoxy)-4-hydroxy-3-nitro-8-n-propyl-coumarin 7-(2-[4-Acetyl-3-hydroxy-6-nitro-2-n-propylphenoxyethoxy]-4-hydroxy-3-nitrocoumarin, and 7-(3-[4-Acetyl-3-hydroxy-6-nitro-2-n-propylphenoxy]-2-hydroxy-propoxy)-4-hydroxy-8-methyl-3-nitrocoumarin.

Preferred compounds are:

7-(3-[4-acetyl-3-hydroxy-2-n-propylphenoxy]-propoxy)-4-hydroxy-3-nitrocoumarin 7-(3-[4-acetyl-3-hydroxy-2-n-propylphenoxy]-2-hydroxypropoxy)-4-hydroxy-3-nitrocoumarin 7-(3-[4-acetyl-3-hydroxy-2-n-propylphenoxy]-2-hydroxy propoxy)-4-hydroxy-8-methyl-3-nitrocoumarin 7-(3-[4-acetyl-3-hydroxy-2-n-propylphenoxy]-2-hydroxypropoxy)-4-hydroxy-8-n-propyl-3-nitrocoumarin 7-(3-[2-n-propylphenoxy]-2-hydroxy propoxy-4-hydroxy-3-nitrocoumarin 7-(3-[4-fluorophenoxy]-propoxy)-4-hydroxy-3-nitrocoumarin 7-(3-[2-methyl]propoxy)-4-hydroxy-3-nitrocoumarin 7-(3-[2-n-propyl-4-fluorophenoxy]-2-hydroxy propoxy)-4-hydroxy-3-nitrocoumarin and 4-hydroxy-3-nitro-6-phenoxyhexoxy coumarin The most preferred being the compound:

7-(3-[4-acetyl-3-hydroxy-2-n-propylphenoxy]-2-hydroxypropoxy-4-hydroxy-3-nitro-8-n-propyl coumarin Examples of specific compounds of formula (I) wherein G is nitro, E is covalent bond and X is methylene are:

5-(2-[4-fluorophenyl]ethoxy)-2-nitroindan-1,3-dione 5-(3-[4-acetylphenyl]propoxy)-2-nitroindan-1,3-dione and 2-nitro-5-(3-[2-n-propylphenyl]butoxy-indan-1,3-dione Examples of specific compounds of formula (I) wherein G is nitro E is a covalent bond and X is oxygen are 2-nitro-5-(3-phenoxypropoxy)indan-1,3-dione 2-nitro-5-(2-phenoxyethoxy)indan-1,3-dione.

2-nitro-5-(5-phenoxypentoxy)indan-1,3-dione 2-nitro-5-(3-[2-n-propylphenoxy]-propoxy)-indan-1,3-dione 2-nitro-5-(2-hydroxy-3-[2-n-propylphenoxy]-propoxy)-indan-1,3-dione 5-(3-[4-acetyl-3-hydroxy-2-n-propylphenoxy]-2-hydroxypropoxy)-2-nitroindan-1,3-dione and 5-(3-[4-acetyl-3-hydroxy-2-n-propylphenoxy]-propoxy)-2-nitroindan-1,3-dione.

The compounds 5-(3-[4-acetyl-3-hydroxy-2-n-propylphenoxy]-2-hydroxypropoxy)-2-nitroindan-1,3-dione, and 5-(3-[4-acetyl-3-hydroxy-2-n-propylphenoxy]-2-hydroxypropoxy-2-nitro-4-n-propylindan-1,3-dione.

are particularly preferred.

Examples of particular compounds of formula (I) falling within the scope of this invention where G is cyano E is oxygen and X is methylene are:

3-cyano-4-hydroxy-6-(2-phenylethoxy) coumarin 3-cyano-4-hydroxy-7-(2-phenylethoxy) coumarin 3-cyano-4-hydroxy-7-(3-phenylpropoxy) coumarin 3-cyano-4-hydroxy-7-(4-phenylbutoxy) coumarin 3-cyano-4-hydroxy-7-(5-phenylpentoxy) coumarin and 5-(3-[4-acetyl-3-hydroxy-2-n-propylphenoxy]butoxy)-3-cyano-4-hydroxy coumarin Examples of compounds of formula (I) falling within the scope of this invention wherein G is cyano, E is oxygen and X is oxygen are:

3-cyano-4-hydroxy-7-(3-[2,3,5-trimethylphenoxy]-propoxy) coumarin 3-cyano-4-hydroxy-7-(3-[4-fluorophenoxy]propoxy) coumarin 7-(3-4-acetyl-3-hydroxy-2-n-propylphenoxy]-2-hydroxypropoxy)-3-cyano-4-hydroxy coumarin 7-(3-[4-acetyl-3-hydroxy-2-n-propylphenoxy]propoxy)-3-cyano-4-hydroxy coumarin and 7-(3-[4-acetyl-3-hydroxy-2-n-propoxyphenoxy]propoxy)-3-cyano-4-hydroxy-8-n-propyl coumarin Examples of compounds of formula (I) where G is cyano, E is a covalent bond and X is methylene are:

2-cyano-5-(2-phenylethoxy)indan-1,3-dione 2-cyano-5-(3-phenylpropoxy)indan-1,3-dione and 2-cyano-5-(4-[4-acetyl-3-hydroxy-2-n-propyl-phenyl]butoxy)-indan-1,3-dione Examples of compounds of formula (I) where G is cyano, E is a covalent bond and X is oxygen are:

2-cyano-5-(3-[2,3,5-trimethylphenoxy]propoxy)indan-1,3-dione 5-(3-[4-acetyl-3-hydroxy-2-n-propylphenoxy]propoxy)-2-cyanoindan-1,3-dione 5-(3-[4-acetyl-3-hydroxy-2-n-propylphenoxy]-2-hydroxypropoxy)-2-cyanoindan-1,3-dione 2-cyano-5-methyl-6-(3-phenoxypropoxy) -indan-1,3-dione.

From the discussion of tautomeric forms it will be appreciated that the bicyclic system includes an acidic 1,3-dicarbonyl This system is capable of forming salts with cationic species. Where it is required to use a compound of formula (I) for medicinal purposes in the form of a salt it is salified with a pharmaceutically acceptable cation.

Examples of suitable salts of the compounds of formula (I) are alkali metal salts particularly sodium and potassium, alkaline earth metal salts such as calcium and magnesium, the aluminium salt and salts with organic bases such as amines or amino compounds, for example N-methyl-D-glucamine.

Where the phenyl ring of substituent (II) contains amino groups these will be able to form acid addition salts with suitable pharmaceutically acceptable anionic species. Examples include the chloride, bromide, sulphate and citrate.

For the purpose of administration, the compounds of this invention may be presented in several dosage forms.

According to this invention there is also provided a pharmaceutical composition having SRS-A inhibiting activity, comprising a compound of formula (I) as defined above or a pharmaceutically acceptable salt thereof, together with a pharmaceutically acceptable carrier.

Examples and preferred values of $A_1$, $A_2$ and $R_1$ to $R_7$ are as previously discussed.

The compositions of this invention may be presented as a microfine powder for insufflation (in such a case the particles of active compound suitably have diameters of less than 50 microns, preferably less than 10 microns) or in the form of an aerosol or a solution for a nebulizer. The compositions may also be presented with a sterile liquid carrier for injection, or in an ointment, cream, lotion or a solution for topical application, or as suppositories.

Compounds of formula (I) which are active when given by the oral route, may be compounded in the form of syrups, tablets, capsules, pills and the like. Preferably the compositions are in unit dosage form, or in a form in which the patient can administer to himself a single dose. For example, when the composition is in the form of a tablet, pill, linguet, powder, troche or lozenge, any suitable pharmaceutical carrier may be used for formulating solid compositions, for example, magnesium sterate, starch, lactose, glucose, rice, flour and chalk. The composition may also be in the form of an ingestible capsule (e.g. of gelatin) to contain the compound, or in the form of a syrup, a liquid solution or a suspension. Suitable liquid pharmaceutical carriers include ethyl alcohol, glycerine, saline and water together with flavouring or colouring agents to form syrups. A suitable dosage unit might contain from 0.1 to 500 mg of active ingredient. The effective dose of compound (I) depends on the particular compound employed, but is in general in the range of from 0.01 mg/kg/day to 100 mg/kg of body weight per day.

Where appropriate, small amounts of anti-asthmatics and bronchodilators, for example sympathomimetic amines such as isoprenaline, isoetharine, salbutamol, phenylephrine and ephedrine; xanthine derivatives such as theophylline and aminophylline; corticosteriods such as pednisolone and adrenal stimulants such as ACTH may be included. As is common practice, the compositions will usually be accompanied by written or printed directions for use in the medical treatment concerned, in this case as an anti-allergic for treatment of, for example asthma, hay-fever or rhinitis.

Compounds of formula (I) where G is nitro may be prepared by reacting a compound of formula (III) or a salt thereof:

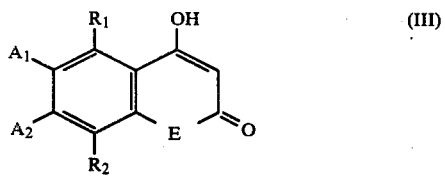

wherein $A_1$, $A_2$, $R_1$ and $R_2$ are as defined above with respect for formula (I), with a nitrating agent. This method is a further aspect of the invention. Nitration may be effected by any conventional nitrating agent for example:

(i) acetic acid and concentrated nitric acid or
(ii) fuming nitric acid in chloroform and/or ether.

The temperature at which the reaction is performed is dependent upon the nitrating reagent employed. In order to avoid nitration of the phenyl ring of the substituent of formula (II):

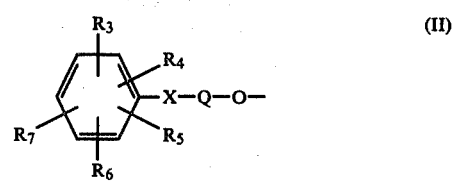

it is most preferable to use a temperature of less than 10° C. and a reaction time up to 90 minutes.

Prefeably the nitrating agent is fuming nitric acid in chloroform and the reaction is performed at a temperature range from −5° C., to +5° C., most preferably at 0° C., for between 15 and 90 minutes.

Where the intermediate is of formula (III) in which E is oxygen and the phenyl ring of the substituent of formula (II) bears one or more electron donating substituents, then it is possible to introduce a nitro group into the phenyl ring and the nucleus in the same reaction.

Accordingly, this invention also provides a method for preparing a compound of formula (I) which process comprises reacting a compound of formula (III) wherein $R_1$, $R_2$, $A_1$ and $A_2$ are as previously defined with reference to formula (I) and $R_3$ to $R_7$ of the substituent (II)

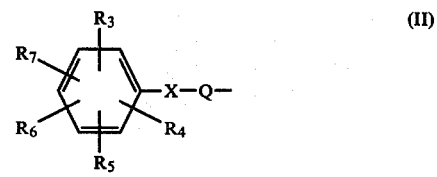

are as defined with respect for formula (I) provided that at least one of $R_3$ to $R_7$ are hydrogen and at least one of $R_3$ to $R_7$ is an electron donating group.

Examples of electron donating groups include lower alkyl, lower alkenyl, lower alkynyl, and lower alkoxy.

In these circumstances the reaction is carried out with a large excess of nitric acid at a temperature from 0° to room temperature and for a period in excess of 90 minutes.

Alternatively, the compounds of formula (I) where E is oxygen and G is nitro excluding those bearing an amino group or substituted amino group in the phenyl ring of substituent (II) may be prepared by nitrosation of the intermediates of formula (III) and subsequently oxidizing the resultant nitroso compound.

Accordingly, also included within the scope of this invention is a process for the preparation of the compound of formula (I) which process comprises nitrosation of a compound of formula (III) wherein $R_1$, $R_2$, $A_1$ and $A_2$ are as defined with respect to formula (I), provided that none of $R_3$ to $R_7$ represent amino or a substituted amino group, with an alkali metal nitrite in the presence of a lower alkanoic acid and thereafter oxidizing the nitroso compound.

The nitrosation reaction is performed in a polar solvent at a temperature between room temperature and 60° C. Suitably the alkali metal nitrite is sodium or potassium nitrite. And suitably the lower alkanoic is acetic acid. Suitably the oxidation step may be performed in situ by rapidly stirring or rapidly passing air through the nitrosation product.

Compounds of formula (I) wherein G is nitro and E is a bond may be prepared by a base catalysed re-arrangement of the corresponding nitromethylene phthalide derivative.

Accordingly the invention also provides a process for preparing a compound of formula (I) and pharmaceutically acceptable salts thereof; which process comprises reacting a compound of formula (IV):

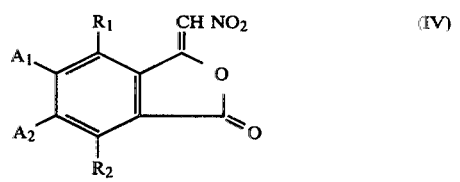

wherein $R_1$, $R_2$, $A_1$ and $A_2$ are as defined with respect to formula (I) with a tertiary base, in the presence of an aprotic solvent and thereafter where desired converting the product thus formed into a pharmaceutically acceptable salt.

By a tertiary base we mean a tertiary amine or heterocyclic aromatic amine.

Suitable tertiary bases include pyridine, picoline and tri-lower alkyl amines such as triethyl amine which is preferred.

Suitable aprotic solvents include halogenated hydrocarbons such as chloroform and carbontetrachloride, and other conventional inert solvents such as lower alkyl ethers, dioxan and tetrahydrofuran. Alternatively the solvent may be the base itself.

Most suitably the reaction is carried out at room temperature.

A suitable method for the preparation of the intermediates (III) where E is oxygen is the condensation of an appropriately substituted o-hydroxyacetophenone (V) with diethyl carbonate in the presence of sodium hydride.

The desired substituent (II) is introduced into an appropriate dihydroxyacetophenone (VI) by coupling with a halide for example, a chloride or bromide of the general formula ArY in the presence of potassium carbonate in acetone as shown in scheme 1. In scheme 1 $R_1$ and $R_2$ are as defined with reference to formula (I) and A represents the one of $A_1$ or $A_2$ which does not represent the substituent of formula (II). Ar signifies a group of formula

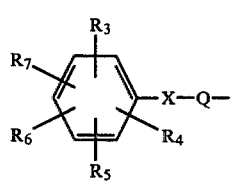

and Y is chlorine or bromine.

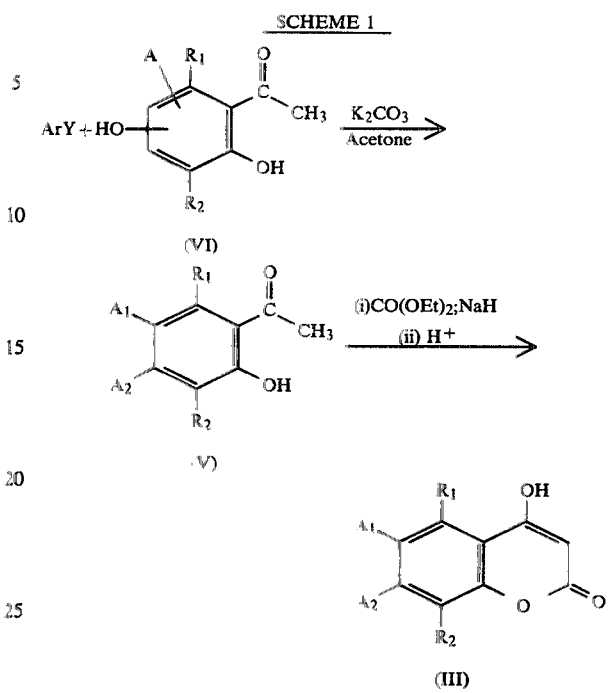

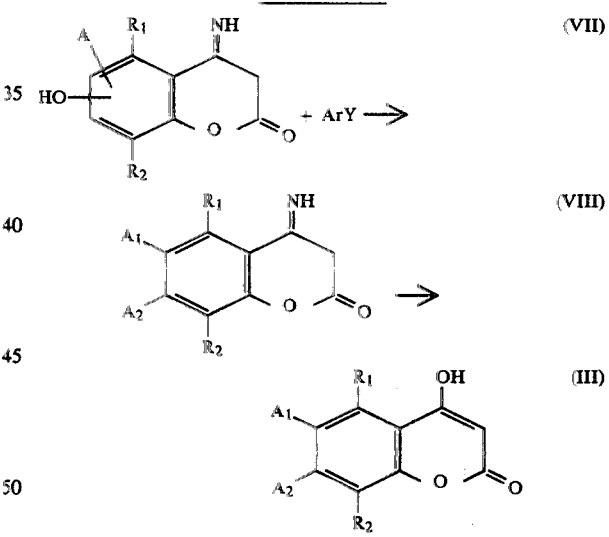

Another suitable method for the preparation of intermediates of the formula (III) where E is oxygen is as shown in Scheme 2 to couple halide ArY with a hydroxy-4-imino-coumarin (VII) using sodium hydride in dimethyl formamide (DMF). The resultant 4-iminocoumarin (VIII) is subsequently hydrolysed to the corresponding 4-hydroxycoumarin (III) with strong acid. The hydroxy-4-imino-coumarins (VII) are made by standard methods. For example, 7-hydroxy-4-iminocoumarin is made from ethylcyanoacetate and resorcinol. This method is particularly useful for the preparation of 7-aryloxy alkyleneoxy coumarins of the general formula (IX):

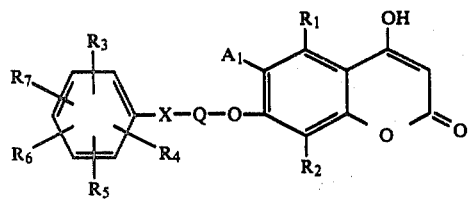

(IX)

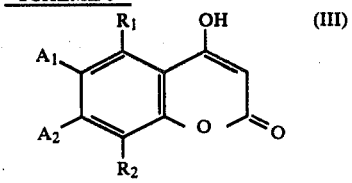

(III)

wherein X, Q, $A_1$ and $R_1$ to $R_7$ are as defined with respect to formula (I) above, especially when Q is substituted by hydroxyl.

A further method for the preparation of intermediates of the formula (III) is shown in the Scheme 3. A halide ArY for example a chloride is coupled with a hydroxy-4-benzyloxycoumarin (X) using sodium hydride in dimethyl formamide (DMF).

Alternatively, where Y is bromine the reaction may be performed using potassium carbonate in acetone or butanone. The resultant 4-hydroxycoumarin is obtained after removal of the benzyl group by hydrogenation with hydrogen and palladium. In the scheme $R_1$, $R_2$, A, $A_1$, $A_2$ and Ar are as defined with reference to scheme 1 and Bz means benzyl.

Alternatively the intermediate (III) may be made by coupling an epoxide of the formula (XII) with either a 4-iminocoumarin of formula (VII) or 4-benzyloxycoumarin of formula (X). These two routes are illustrated in Scheme 4 below. The 4-hydroxycoumarin of formula (XIII) is liberated either by hydrolysis of the iminocoumarin (XIV) or hydrogenolysis of the benzyloxycoumarin (XV). This 4-hydroxycoumarin falls within the definition of formula (IV). In Scheme 4 the symbols are as previously defined in the text and n is an integer from 1 to 4.

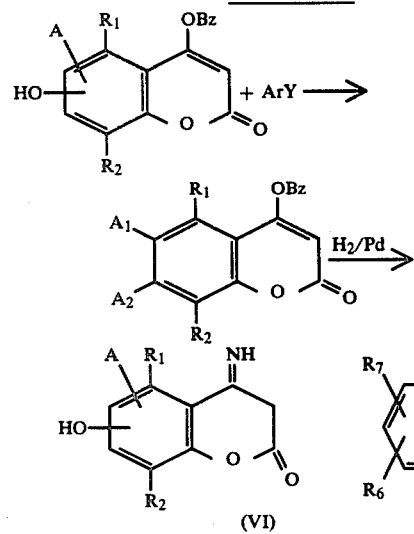

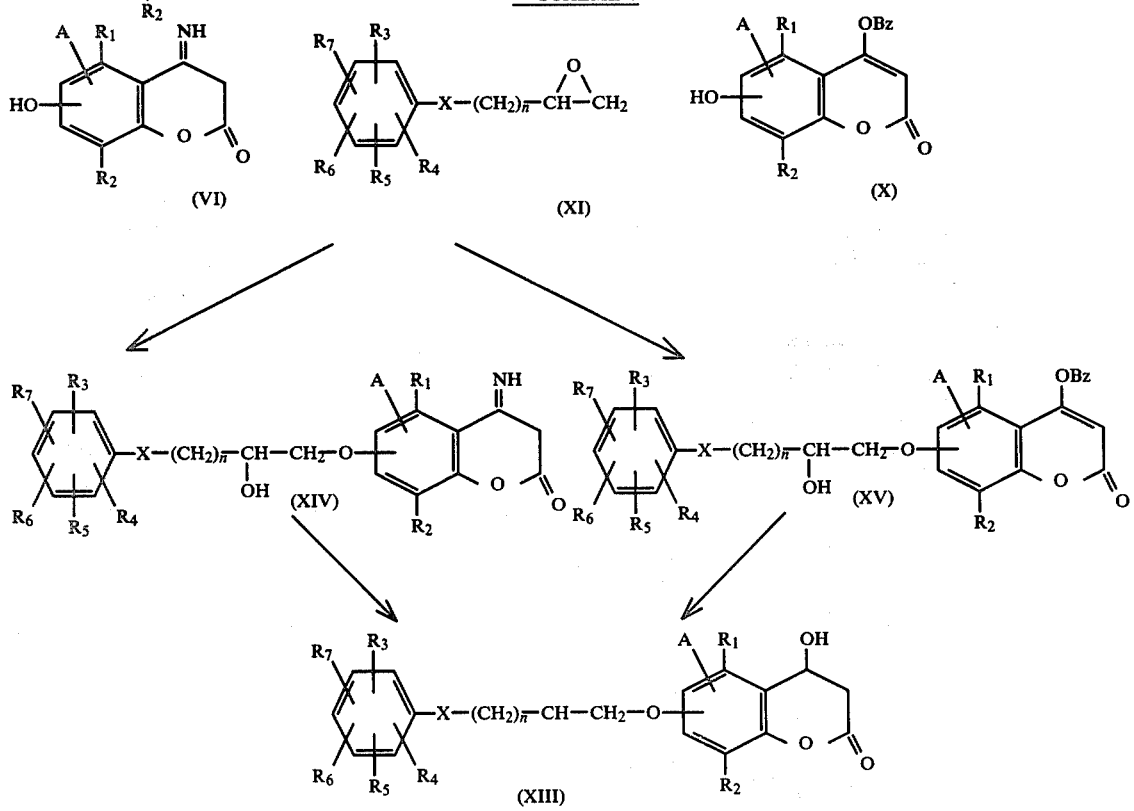

The intermediates of formula (IV) are prepared by coupling a suitable halide ArY with a dimethyl hydroxyphthalate (XVI) using a suitable base such as potassium carbonate and converting the resulting ester (XVII) to the anhydride (XVIII). This anhydride is then converted with nitromethane and base, to the 2-nitroacetylbenzoic acid derivative (XIX) which is then dehydrated.

This is illustrated in Scheme 5 below:

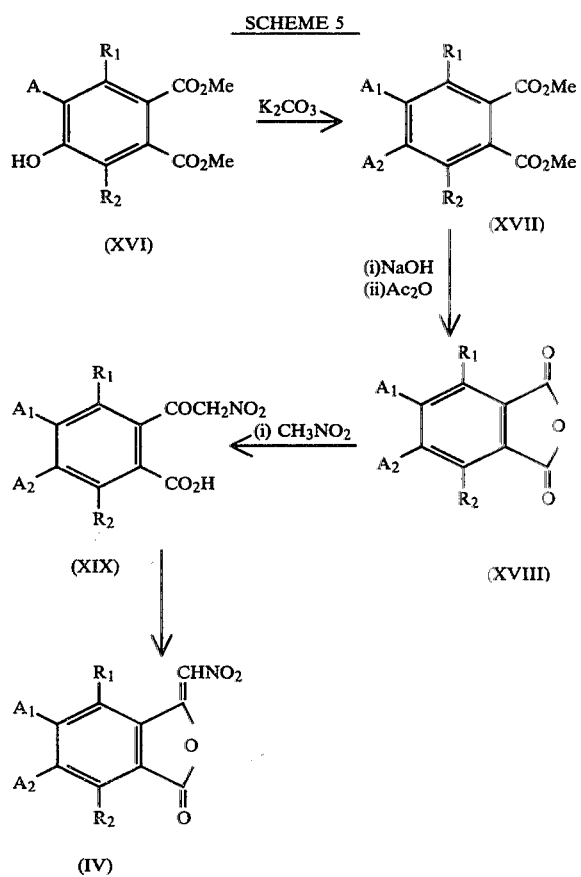

The compounds of formulae (XVIII) and (IV) prepared in this sequence will be in isomeric mixture as shown. This mixture may be used without separation since both isomers give the same 2-nitroindan-1,3-dione. Where the halide ArY contains active groups such as hydroxy or acetyl which may interfere with the coupling reaction these are optionally protected with standard protecting groups.

Where the substituent A contains groups which are susceptible to acylation, the dehydration reaction is carried out with a mild dehydrating reagent such as NN'-dicyclohexylcarbodiimide.

A further suitable method for the preparation of the intermediate (IV) is to couple the aralkyl-halide Ar Y to a hydroxynitromethylenephthalide (XX)

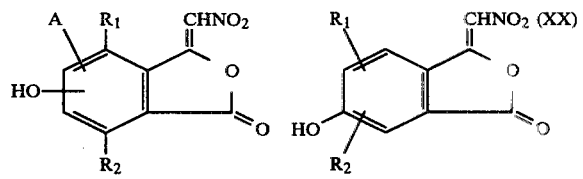

by a method analogous to that for the preparation of the diester (XVII). This method is also particularly suitable where the substituent A contains groups susceptible to acylation.

The intermediate (III) where E is a bond may be prepared by condensing the diester (XVII) with ethylacetate and strong base. Where the substituent A of the diester (XVII) contains active groups such as hydroxy and/or acetyl which would interfere with the condensation reaction these are optionally protected by conventional protecting groups which are removed after the indan-1,3-dione nucleus has been formed.

The diester of formula (XVII) and the intermediates of formulae (IV) in which the alkylene chain Q of the substituent II includes a hydroxyl group, may be prepared by coupling either the dimethyl hydroxy phthalate (XVI) or the hydroxy nitromethylenephthalides (XX) with epoxide (XII).

This coupling reaction is carried out in a polar aprotic solvent such as dimethylformamide (DMF) in the presence of a strong base such as sodium hydride. If the epoxide contains any activated substituents such as acetyl and/or hydroxy which may interfere in the coupling reaction these are optionally protected with standard protecting groups.

Compounds of formula (I) where G is cyano and E is oxygen and their salts are prepared by reacting an activated carbonyl compound of the formula (XXI)

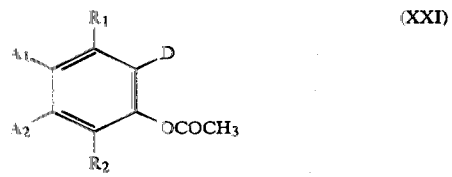

wherein $R_1$ and $R_2$, $A_1$ and $A_2$ are as previously defined and D represents an activated carbonyl group, with a carbanion of formula $NC-C^{\ominus}H-R$, wherein R represents a carboxylic acid ester group, and thereafter where desired converting the compound of formula (I) thus formed, to a salt.

The carbanion may be prepared by the reaction of the compound $NC-CH_2-R$ with a base. Suitable bases for this purpose are sodium ethoxide and sodium hydride.

The group D represents an activated carbonyl of formula COZ where Z is chlorine or bromine, or the residue of a mixed anhydride. Z preferably represents chlorine.

The nature of the carboxylic ester group R is not critical to the success of the reaction, but we have found that alkyl esters, wherein the alkyl moiety contains one to four carbon atoms, such as the ethyl ester, are particularly suitable.

The reaction is preferably carried out in an inert, anhydrous solvent. Suitable solvents include simple ethers such as diethylether, dioxan and tetrahydrofuran.

The compounds of formula (XXI) are prepared from dihydroxy benzoic acid esters of formula (XXII) as shown in scheme 6 below wherein A, $A_1$, $A_2$, $R_1$, $R_2$ and ArY are as defined in Scheme 1.

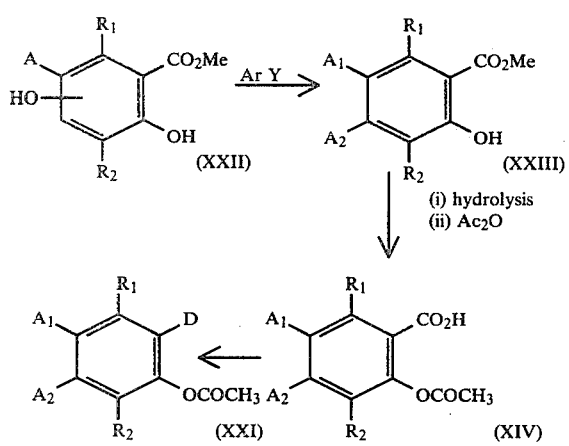

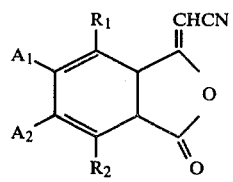

The substituent of formula (II) is introduced by coupling the halide Ar Y where Y is chlorine, bromine or iodine, with the methyl dihydroxybenzoate of formula (XXII). The methyl hydroxy benzoate of formula (XXIII) is hydrolysed and acylated, and the free acid group is then converted to a suitable activated carbonyl derivative such as an acyl halide, with a suitable halogenating agent such as thionyl chloride or bromide, or to an activated anhydride.

Compounds of the formula (I) and their salts wherein E is a bond and G is cyano are prepared by reacting a compound of formula (XXVI):

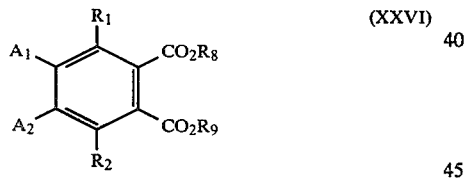

wherein $A_1$, $A_2$, $R_1$ and $R_2$ are as defined with respect to formula (I) and $R_8$ and $R_9$ are lower alkyl groups, with acetonitrile in the presence of a base, and thereafter where desired converting the compound of formula (I) to a salt.

Suitable bases include alkali metal hydrides, in particular sodium hydride, and alkali metal and alkaline earth metal salts of lower alkanols; in particular sodium methoxide and ethoxide. $R_8$ and $R_9$ are suitably methyl or ethyl.

The intermediates (XXVI) may be prepared by an alkylation method analogous to that for the preparation of the compounds of formula (XVII).

Alternatively, the compounds of formula (I) wherein E represents a bond may be prepared by rearranging a cyanomethylene-phthalide (XXVII).

wherein $A_1$, $A_2$, $R_1$ and $R_2$ are as defined with respect to formula (I) with a base, and thereafter where desired converting the compound of formula (I) thus formed to a salt.

The most suitable bases for this purpose are alkali metal and alkaline earth metal lower alkoxides. The intermediates of formula (XXVII) may be prepared by hydrolysing and dehydrating the ester (XXVI) to form the corresponding phthalic anhydride, which is then reacted with cyanoacetic acid and a tertiary base such as pyridine.

Alternatively, the intermediates (XXVII) may be prepared from a suitable azido naphthaquinone (XXVIII).

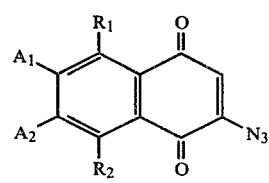

by the method analogous to that disclosed in our Offenlegungsschrift No. 2,519,713.

It is to be understood that suitable and preferred definition for $A_1$, $A_2$ and $R_1$ to $R_7$ when representing substituents on compounds of formula (I) apply equally to $A_1$, $A_2$ and $R_1$ to $R_7$ when representing substituents on the intermediates (III) (IV) (XXI) (XXVI) and (XXVII) in the foregoing discussion.

The following examples illustrate the preparation and properties of some compounds falling within the scope of this invention.

EXAMPLES

EXAMPLE 1

2-Hydroxy-4-(3-phenoxypropoxy) acetophenone

A mixture of 1-bromo-3-phenoxypropane (21.5 g; 0.1 mole), 2,4-dihydroxyacetophenone (15.2 g; 0.1 mole) and anhydrous potassium carbonate (20.8 g; 0.15 mole) in dry acetone (300 ml) was stirred at reflux for 24 hours when tlc indicated complete reaction. After cooling the potassium salts were removed by filtration and the filtrate evaporated to a pink solid. Recrystallisation from ethanol in the presence of charcoal gave 21.94 g (77%) of a white solid of tlc purity, m.p. 82°–82.5°; $\nu$max (mull) 1618, 1600, 1595 cm$^{-1}$; $\tau$(CDCl$_3$); 7.73(2H, quintet, J 6.3 Hz); 7.48(3H, s); 5.85(2H, t, J 6.3 Hz); 5.79(3H t, J 6.3 Hz); 3.54(2H, m); 3.22–2.38(5H, complex m); 2.37(1H, d, J 9.5 Hz); 1 low field exchangeable proton. (Found: C, 71.28; H, 6.58; $C_{17}H_{18}O_4$ requires; C, 71.31; H, 6.34%).

In a similar manner were made the examples in Table 1.

TABLE I

| Example | Compound | m.p. °C. | Yield % | Analysis |
|---|---|---|---|---|
| 2 | 2-Hydroxy-4-(2-phenyl-ethoxy) acetophenone | 69 | 45 | Found; C, 74.80; H,6.17; $C_{16}H_{16}O_3$ requires; C, 74.98; H,6.29 |
| 3 | 2-Hydroxy-5-(2-phenyl-ethoxy) acetophenone | 36 | 21 | Found; C, 74.99; H,6.35; $C_{16}H_{16}O_3$ requires; C,74.98; H,6.29 |
| 4 | 2-Hydroxy-4-(3-phenyl-propoxy) acetophenone | 74–77 | 83 | Found; C, 75.47; H,6.87; $C_{17}H_{18}O_3$ requires; C, 75.53; H,6.71 |
| 5 | 2-Hydroxy-5-(3-phenyl-propoxy) acetophenone | 34–35 | 54 | Found; C,75.82; H,6.90; $C_{17}H_{18}O_3$ requires; 75.53; H, 6.71 |
| 6 | 2-Hydroxy-4-(4-phenyl-butoxy) acetophenone | 55 | 59 | Found; C, 75.95; H,7.00; $C_{18}H_{20}O_3$ requires; C, 76.03; H,7.09 |
| 7 | 4-(4-chlorophenyl] butoxy)-2-hydroxy-acetophenone | 73–75 | 71 | Found; C, 68.17; H,6.33; Cl,11.25; $C_{18}H_{19}ClO_3$ requires; C, 67.81; H,6.01; Cl, 11.12 |
| 8 | 2-Hydroxy-4-(4-[4-methyl-phenyl]butoxy) acetophene | 69–70 | 72 | Found; C, 76.22; H, 7.59; $C_{19}H_{22}O_3$ requires; C, 76.57; H, 7.38 |
| 9 | 2-Hydroxy-4-(2-phenoxy-ethoxy) acetophenone | 113–134 | 62 | Found; C, 70.49; H, 6.00; $C_{16}H_{16}O_4$ requires; C,70.57; H, 5.92 |
| 10 | 2-Hydroxy-5-(2-phenoxy-ethoxy) acetophenone | 133–114 | 43 | Found; C, 70.58; H, 5.94; $C_{16}H_{16}O_4$ requires; C, 70.57; H, 5.92 |
| 11 | 2-Hydroxy-5-(3-phenoxy-ethoxy) acetophenone | 87–88 | 70 | Found; C, 71.34; H, 6.50; $C_{17}H_{18}O_4$ requires; C, 71.31; H, 6.34 |
| 12 | 2-Hydroxy-4-(4-phenoxy-butoxy) acetophenone | 95–96 | 87 | Found; C, 72.06; H, 6.83; $C_{18}H_{20}O_4$ requires; C, 71.98; H, 6.71 |
| 13 | 2-Hydroxy-4-(5-phenoxy-pentoxy) acetophenone | 51–52 | 62.5 | Found; C, 72.34; H, 7.07; $C_{19}H_{22}O_4$ requires; C, 72.59; H, 7.05 |
| 14 | 2-Hydroxy-5-(5-phenoxy-pentoxy) acetophenone | 45 | 78 | Found; C, 72.77; H, 7.21; $C_{19}H_{22}O_4$ requires; C, 72.59; H, 7.05 |
| 15 | 2-Hydroxy-4-(6-phenoxy-hexoxy) acetophenone | 71–74 | 69 | Found; C, 72.98; H, 7.16; $C_{20}H_{24}O_4$ requires; C, 73.15; H, 7.37 |
| 16 | 2-Hydroxy-5-(6-phenoxy-hexoxy) acetophenone | 78 | 43 | Found; C, 71.80; H, 7.31; $C_{20}H_{24}O_4$ requires; C, 73.15; H, 7.37 |
| 17 | 4-(3-[4-chlorophenoxy-acetophenone | 82–83 | 80 | Found; C, 63.36; H, 5.41; Cl, 10.99; $C_{17}H_{17}ClO_4$ |
| 18 | 2-Hydroxy-4-(3-[4-methyl-phenoxy]propoxy) aceto-phenone | 85–87 | 67 | Found; C, 72.32; H, 7.01; $C_{18}H_{20}O_4$ |
| 19 | 2-Hydroxy-4-(3-[3-methyl-phenoxy]propoxy) aceto-phenone | 64 | 80 | Found; C, 71.93; H, 6.95; $C_{18}H_{20}O_4$ requires; C, 71.98; H, 6.71 |
| 20 | 2-Hydroxy-4-(3-[2-methyl-phenoxy]propoxy) aceto-phenone | 64 | 65 | Found; C, 72.28; H, 6.77; $C_{18}H_{20}O_4$ requires; C, 71.98; H, 6.71 |
| 21 | 2-Hydroxy-4-(3-[4-methoxyphenoxy]propoxy) acetophenone | 75–76 | 59 | Found; C, 68.14; H, 6.51; $C_{18}H_{20}O_5$ requires; C, 68.34; H, 6.37 |
| 22 | 4-(3-[4-Fluorophenoxy] propoxy)-2-hydroxyaceto-phenone | 70–72 | 59 | Found; C, 67.24; H, 5.61; $C_{17}H_{17}FO_4$ requires; C, 67.11; H, 5.59 |
| 23 | 4-(3-[4-Cyanophenoxy] propoxy)-2-hydroxyaceto-phenone | 131–133 | 65 | Found; C, 69.26; H, 5.67; N, 4.22; $C_{18}H_{17}NO_4$ requires; C, 69.45; H, 5.47; N, 4.50 |
| 24 | 2-Hydroxy-4-(3-[4-phenylphenoxy]propoxy) acetophenone | 181–121 | 72 | Found; C, 76.32; H, 6.44; $C_{23}H_{22}O_4$ requires; C, 76.24; H, 6.08 |
| 25 | 2-Hydroxy-4-(3-[5,6,7,8-tetrahydro-2-naphtyloxy] propoxy) acetophenone | 80–82 | 59 | Found; C, 74.11; H, 7.11; $C_{21}H_{22}O_4$ requires; C, 74.12; H, 7.06 |
| 26 | 2-Hydroxy-4-(3-phenoxy-propoxy)-3-n-propyl-acetophene | 67–68 | 84 | Found; C, 73.05; H, 7.57; $C_{20}H_{24}O_4$ requires; C, 73.15; H, 7.37 |
| 27 | 5-Ethyl-2-hydroxy-4-(3-phenoxypropoxy) aceto-phenone | 60.5–61.5 | 74 | Found; C, 72.45; H, 7.20; $C_{19}H_{22}O_4$ requires; C, 72.59; H, 7.05 |

EXAMPLE 28

1-Chloro-3-phenoxy-2-propanol

A mixture of phenol (94 g; 1.0 mole) and epichlorhydrin (138.8 g; 1.5 mole) was vigorously stirred at 100° C. in the presence of piperidine hydrochloride (2.0 g) for 6 hours, cooled, and the excess epichlorohydrin removed at 100° in vacuo. The residue was cooled, dissolved in an equal volume of chloroform and stirred vigorously with excess concentrated hydrochloric acid for 0.5 hours. After separation of the phases the organic layer was washed with water, dried and evaporated to a colourless oil. Distillation gave 116.4 g (62.5%) of 1-chloro-3-phenoxy-2-propanol of bp$_{0.6}$ 112° as a GLC pure material, $\nu$max (film) 3310, 1603, 1590, 1495, 1245 cm$^{-1}$; $\tau$(CDCl$_3$); 7.40 (broad exchangeable s); 6.25 (2H, d, J 3.5 Hz); 5.90 (2H, s); 5.90 (1H, m); 3,21–2.56 (5H, m).

Similarly were prepared the compounds of Table II.

EXAMPLE 38

3,4-Dihydro-7-(2-hydroxy-3-phenoxypropoxy)-4-iminocoumarin

To a warm stirred suspension of 3,4-dihydro-7-hydroxy-4-iminocoumarin (17.7 g; 0.1 mole) in dry DMF (75 ml) was added sodium hydride (2.4; 0.1 mole) portionwise and the mixture refluxed for 1.5 hours to complete formation of the sodium salt. A solution of 1-chloro-3-phenoxy-2-propanol (18.7 g; 0.1 mole) in dry DMF (10 ml) was added dropwise at reflux and the mixture stirred at reflux for an additional 4 hours. The solvent was removed in vacuo and water (200 ml) added to the residue. The yellow solid was filtered off, washed well with water and dried in vacuo over P$_2$O$_5$ to give 30.0 g (92%) of crude product which was suitable for most purposes. Recrystallisation from ethyl acetate gave material of m.p. 213°–214°; $\nu$max (mull) 3320, 3200, complex carbonyl region 1690–1590 cm$^{-1}$, $\tau$(DSMO); 5.82(5H, m); 5.35(2H, broad exchangeable

TABLE II

| Example | Compound | m.p. or b.p. °C. | Yield % | Analysis |
|---|---|---|---|---|
| 29 | 1-Chloro-3-(2-n-propyl-phenoxy)-2-propanol | bp$_{2.0}$ 136–140 | 44 | |
| 30 | 1-(4-Acetyl-2-n-propyl-phenoxy)-3-chloro-2-propanol | oil | 100 | Found; C, 61.32; H, 7.01; Cl, 14.02; C$_{14}$H$_{19}$ClO$_3$ requires; C, 62.10; H, 7.07; Cl, 13.10 |
| 31 | 1-(4-Acetyl-3-hydroxy-phenoxy)-3-chloro-2-propanol | oil | 60 | |
| 32 | 1-(4-Acetyl-3-hydroxy-2-methylphenoxy)-3-chloro-2-propanol | m.p. 112–116 | 63 | Found; C, 55.90; H, 6.09; Cl, 13.79; C$_{12}$H$_{15}$ClO$_4$ requires; C, 55.71; H, 5.84; Cl, 13.71 |
| 33 | 1-Chloro-3-(4-Fluoro-2-n-propylphenoxy)-2-propanol | bp$_{0.6}$ 123–127 | 73 | Found; C, 58.27; H, 6.8, Cl, 14.39; C$_{12}$H$_{16}$ClFO$_2$ requires; C, 58.42; H, 6.54; Cl, 14.37 |
| 34 | 1-(4-Acetyl-2-allyl-3-hydrophenoxy)-3-chloro-2-propanol | m.p. 100–104 | 61 | Found; C, 58.78; H, 6.08; Cl, 13.19; C$_{14}$H$_{17}$ClO$_4$ requires; C, 59.05; H, 6.02; Cl, 12.45 |
| 35 | 1-(2-Allyl-3-hydroxy-4-proprionylphenoxy)-3-chloro-2-propanol | oily-solid | 100 | Found; C, 60.17; H, 6.44; Cl, 12.23; C$_{15}$H$_{19}$ClO$_4$ requires; C, 60.30; H, 6.41; Cl, 11.87 |
| 36 | 1-(4-Acetyl-2-ethyl-5-hydroxyphenoxy)-3-chloro-2-propanol | bp$_{1.5}$ 220 m.p. 65 | 74 | Found; C, 57.36; H, 6.37; Cl, 12.93; C$_{13}$H$_{17}$ClO$_4$ requires; C, 57.25; H, 6.28; Cl, 13.00 |
| 37 | 1-(4-Carbomethoxy-phenoxy)-3-chloro-2-propanol | bp$_{0.5}$ 170–172 | 75 | Found; C, 54.30; H,5.51; Cl, 14.17; C$_{11}$H$_{13}$ClO$_4$ requires; C,54.03; H, 5.36; Cl 14.49 | s); 4.85(1H, s); 3.20–2.52(8H, m with 1 proton removed after D$_2$O exchange); 2.02(1H, d,) (Found; C, 64.52; H, 5.26; N, 3.78; C$_{18}$H$_{17}$NO$_5$ 0.5H$_2$O requires; C, 64.28; H, 5.39; N, 4.16%).

By the same procedure the compounds in Table III were prepared.

TABLE III

| Example | Compound | m.p. °C. | Yield % | Analysis |
|---|---|---|---|---|
| 39 | 7-(3-[4-Acetyl-3-hydroxy]propoxy)-3,4-dihydro-4-iminocoumarin | 158–159 | 60 | Found; C, 64.90; H, 5.54; N, 3.49; C$_{20}$H$_{19}$NO$_6$ requires; C, 65.03; H, 5.18; N, 3.79 |
| 40 | 7-(3-[4-Acetylphenoxy]-propoxy)-3,4-dihydro-4- | 165–168 | 94 | Found; C, 67.59; H, 5.54; N, 3.92; C$_{20}$H$_{19}$NO$_5$ |

TABLE III-continued

| Example | Compound | m.p. °C. | Yield % | Analysis |
|---|---|---|---|---|
| | iminocoumarin | | | requires; C, 67.98; H, 5.42; N, 3.96 |
| 41 | 3,4-Dihydro-5-methyl-7-(3-phenoxypropoxy)-4-iminocoumarin | 164–167 | 91 | Found; C, 69.81; H, 6.12; N, 3.96; $C_{19}H_{19}NO_4$ requires; C, 70.14; H, 5.89; N, 4.30 |
| 42 | 7-(3-[4-Carbomethoxy-phenoxy]propoxy)-3,4-dihydro-4-iminocoumarin | 155 | 100 | Found; C, 62.40; H, 5.49; N, 3.39; $C_{20}H_{19}NO_6H_2O$ requires; C, 62.01; H, 5.46; N, 3.62 |
| 43 | 7-(3-[4-Carbomethoxy-phenoxy]-2-hydroxypropoxy)3,4-dihydro-4-iminocoumarin | 212–215 | 94 | Found; C, 58.98; H, 5.04; N, 3.58; $C_{20}H_{19}NO_7H_2O$ requires; C, 59.55; H, 5.25; N, 3.47 |

EXAMPLE 44

4-Benzyloxy-7-hydroxycoumarin

A solution of 4,7-dihydroxycoumarin (1.78 g, 0.01 mole) in dry DMF (7.5 ml) was stirred during the addition of 100% sodium hydride (0.24 g, 0.01 mole) and the mixture stirred for 1 hour at 100°. A solution of benzyl chloride (1.27 g, 0.01 mole) in dry DMF (1 ml) was added dropwise and stirring continued at 100° for a further 4 hours. After removal of the solvent in vacuo water was added and the oily solid which precipitated was separated. Recrystallisation from ethanol gave 0.623 g (23%) of title compound of m.p. 234° $\nu$max (mull) 3150, 3050, 1710, 1630 cm$^{-1}$, $\tau$(DMSO) 4.67 (2H, s); 4.19 (1H, s); 3.28 (1H near s); 3.20 (1H, d.d., J 2.0 Hz; 5.0 Hz) 2.66–2.26 (6H, m), 1 low field broad exchangeable proton. (Found, C, 71.51; H, 4.70; $C_{16}H_{12}O_4$ requires; C, 71.64; H, 4.51%).

EXAMPLE 45

4-Benzyloxy-7-(2-[4-fluorophenyl]ethoxy) coumarin.

A mixture of 4-benzyloxy-7-hydroxycoumarin (5.36; 0.02 mole) anhydrous potassium carbonate (4.0 g) and 1-bromo-2-(4-fluorophenyl) ethane (4.06 g) in acetone (100 ml) was stirred at reflux for 20 hours and the inorganic material filtered off. Evaporation of the filtrate in vacuo gave an oil which rapidly set solid on scratching. Chloroform (200 ml) was added and the mixture filtered to remove unchanged 4-benzyloxy-7-hydroxycoumarin. Reevaporation of the filtrate afforded a white solid, 3.34 g (43%) of m.p. 120°, $\nu$max (mull) 1715, 1675, 1620 cm$^{-1}$; $\tau$(CDCl$_3$); 6.93 (2H, t, J 6.7 Hz); 5.80 (2H, t, J 6.7 Hz); 4.87 (2H, S); 4.38 (1H, ); 3.29–2.49 (6H, m) 2.32 (1H, d, J 10 Hz); (Found C, 73.75 H, 5.14 $C_{24}H_{19}FO_4$ requires; C, 73.84; H, 4.91%).

EXAMPLE 46

7-(3-[4-Acetylphenyl]propoxy)-4-benzyloxycoumarin

Alkylation of 4-benzyloxy-7-hydroxycoumarin (2.68; 0.01 mole) with 1-(4-acetylphenyl)-3-bromopropane (2.41 g; 0.01 mole) as described in Example 45 gave 3.28 g (77%) of title compound of m.p. (EtOH) 117° $\nu$max (mull) 1725, 1682, 1620 cm$^{-1}$; $\tau$(DMSO) 7.92 (2H, m); 7.48 (3H, s); 7.18 (2H, m); ;5.94 (2H, t, J 6.4 Hz); 6.69 (2H, s); 6.16 (1H, s); 3.17–2.00 (12H, m). (Found; C, 75.14; H, 5.52; $C_{21}H_{24}O_5$ requires; C, 75.68; H, 5.65%)

EXAMPLE 47

2-Hydroxy-3-n-propyl-4-(tetrahydropyran-3-yloxy) acetophenone

To a mixture of 2,4-dihydroxy-3-n-propylacetophenone (10 g) and dihydropyran (25 ml) was added three drops of concentrated hydrochloric acid. The mixture became warm and solution was attained. After standing at ambient temperature overnight, ether was added and then 2.5 N sodium hydroxide solution. The phases were separated and the aqueous phase extracted with ether. The combined organic phases were washed with water, dried (MgSO$_4$) and evaporated to an oil which was distilled to give 12.05 g (77%) of ether boiling at 152°–172° at 0.4 mm max (film) 2680 (broad) 1725, 1630, 1590, 1494 cm$^{-1}$.

EXAMPLE 48

4-Hydroxy-8-n-propyl-7-(tetrahydropyran-3-yloxy) coumarin

A solution of 2-hydroxy-3-propyl-4-(tetrahydropyran-3-yloxy) acetophenone (12.05 g; 0.043 mole) in dry benzene (100 ml) was added to a stirred suspensions of sodium hydride (2.40 g; 0.1 mole) in dry benzene (100 ml) over 30 mins. at reflux. After a further 10 mins. a solution of diethyl carbonate (10.7 g; 0.087 mole) in benzene (100 ml) was added over 1 hr. and the mixture stirred at reflux over night. Water was added to the cooled solution and the brown aqueous phase washed with ether, cooled to below 5° C. and cautiously acidified. A pale yellow solid separated which was filtered off and washed with water. Recrystallisation afforded 6.986 g (53%) of product of m.p. 163°–165°, $\nu$max (mull) 2710, 2600, 1660, 1630, 1600 cm$^{-1}$ $\tau$(DMSO), 9.08 (3H, t, J 7.0 Hz); 8.34 (8H, m); 7.25 (2H, m); 6.36 (2H, broad); 4.50 (1H, sharp exchangeable s); 4.33 (1H, broad s) 2.62 (2H, AB quartet, J 9.0 Hz; 35 Hz). 1 low field broad exchangeable proton. (Found; C, 67.49; H, ; 6.89; $C_{17}H_{20}O_5$ requires; C, 67.09; H, 6.62%).

EXAMPLE 49

4-Benzyloxy-7-hydroxy-8-n-propylcoumarin

Sodium hydride (0.538; 10% excess) was added to a solution of 4-hydroxy-8-n-propyl-7-(tetrahydropyran-3-yloxy) coumarin (6.08 g; 0.002 mole) in dry DMF (10 ml) and the stirred mixture brought to 100°. A solution of benzyl chloride (2.76 g; 2.5 ml; 10% excess) in dry DMF (2 ml) was added over 30 min. and the mixture kept at 100°–110° for 6 hrs. After cooling the solvent was removed in vacuo and water added. The precipitated sticky solid was taken up on chloroform, washed with dilute sodium hydroxide solution then water and dried. Evaporation gave a pink solid which after recrystallisation from ethanol gave white crystals, 1.533 g (19.5%) of the tetrahydropyranyl ether of the title compound of m.p. 146°–147° νmax (mull) 1735, 1625, 1615 cm$^{-1}$; τ(DSMO) 9.11 (3H, t, J 7.5 Hz); 8.36 (8H, m); 7.28 (2H, t, J 7.5 Hz); 6.44 (2H, m); 4.70 (2H, S); 4.40 (1H, S); 4.18 (1H, S); 2.94 (1H, d, J 9 Hz); 2.58 85H, m); 2.40 (1H, d, J 9 Hz). (Found; C, 73.14; H, 6.78; $C_{24}H_{26}O_5$ requires; C, 73.08; H, 6.64%). The alkaline washings upon acidification gave a brown tar which on dissolution in ethanol deposited the title compound, 0.905 g (15%), on standing. The product had m.p. 213°–214°, νmax (mull) 3050 (broad); 1675, 1605, 1570 cm$^{-1}$; τ(DMSO) 9.09 (3H, t, J 7.5 Hz); 8.46 (2H, p, J & .4 Hz); 7.31 (2H, t J 7.5 Hz); 4.70 (2H, s); 4.22 (1H, S); 3.15 (1H, d, J 9 Hz); 2.56 (6H, m) 1 low field exchangeable proton. (Found; C, 73.54; H, 6.07; $C_{19}H_{18}O_4$ requires; C, 73.53; H, 5.85%).

Decomposition of the tetrahydropyranyl ether isolated from the ethereal phase with methanolic acid gave the title compound in 71% yield, and of m.p. 212°, after recrystallisation.

EXAMPLE 50

7-(3-[4-Acetyl-3-hydroxy-2-n-propylphenoxy]-2-hydroxypropoxy)-4-benzyloxycoumarin A solution of 4-benzyloxy-7-hydroxycoumarin (5.36 g; 6.02 mole) in dry DMF (30 ml) was treated with 100% sodium hydride (0.48 g; 0.02 mole) and stirred at 100° for about 1 hr. To this was added a solution of 1-(4-Acetyl-3-hydroxy-2-n-propylphenoxy)-3-chloro-2-propanol (7 g) in DMF (2 ml) and the mixture stirred at 100° for an additional 4 hrs. After removal of the solvent in vacuo, water was added and the product extracted into chloroform. Chromatography of the extract on 300 g of silica gel eluting with chloroform afforded the title compound as a white crystalline solid of R$_f$0.38. m.p. (EtOH) 172°–173°. Yield 4.38 g (42%). νmax (mull) 1715; 1630; 1620 cm$^{-1}$. (DMSO) 9.19 (3H, t, J 7.0 Hz); 8.58 (2H, sextuplet, J. 7.0 Hz); 7.48 (3H, S+2H m); 6.71 (1H sharp exchangeable); 5.80 (5H, S); 4.68 (2H, S), 4.50 (1H, broad exchangeable); 4.13 (1H, S); 3.32 (1H, d, J 9 Hz); 3.12–2.15 (12H, m); 1 low field sharp exchangeable. (Found: C, 69.30; H, 5.80; $C_{30}H_{30}O_8$ requires; C 69.49; H, 5.83%).

By an analogous procedure, although not always necessitating chromatography, were prepared the compounds listed in Table IV.

TABLE IV

| Example | Compound | m.p. °C. | Yield % | Analysis |
|---|---|---|---|---|
| 51 | 4-Benzyloxy-7-(4-chlorophenoxy-methoxy coumarin | 146–147 | 62 | Found; C, 67.69; H, 4.33; Cl, 8.64; $C_{23}H_{17}ClO_5$ requires; C, 67.57; H, 4.19 Cl, 8.67 |
| 52 | 7-(2-[4-Acetyl-2-hydroxy-3-n-propyl-phenoxy]ethoxy)-4-benzyloxy-coumarin | 175–176 | 41 | Found; C, 71.21; H, 5.80; $C_{29}H_{28}O_7$ requires; C, 71.30; H, 5.78 |
| 53 | 4-Benzyloxy-7-(3-[4-carbomethoxyphenoxy] propoxy) coumarin | 153–155 | 69 | Found; C, 70.42; H, 5.60; $C_{27}H_{24}O_7$ requires; C, 70.43; H, 5.25 |
| 54 | 7-(3-[4-Acetyl-3-hydroxy-2-n-propyl-phenoxy]propoxy)-4-benzyloxy coumarin | 190 | 32 | Found; C, 71.77; H, 6.29; $C_{30}H_{30}O_7$ requires; |
| 55 | 4-Benzyloxy-7-(2-hydroxy-3-[2-n-propylphenoxy] coumarin | 109–110 | 26 | Found; C, 73.04; H, 6.05; $C_{28}H_{28}O_6$ requires; C, 73.04; H, 6.13 |
| 56 | 7-(3-[4-Acetyl-3-hydroxyphenoxy]-2-hydroxypropoxy)-4-benzyloxycoumarin | 192–195 | 33 | crude |
| 57 | 7-(3-[4-Acetyl-2-n-propylphenoxy]-2-hydroxypropoxy)-4-benzyloxycoumarin | 154 | 18 | Found; C, 71.85; H, 6.05; $C_{30}H_{30}O_7$ requires; C, 71.70; H, 6.02 |
| 58 | 7-(3-[4-Acetyl-3-hydroxy-2-methyl-phenoxy]-2-hydroxy-propoxy)-4-benzyloxy-coumarin | 157 | 30 | Found; C, 67.24; H, 5.44; $C_{28}H_{26}O_8 \cdot 0.5H_2O$ requires; C, 67.32; H, 5.45 |
| 59 | 7-(3-[4-Acetyl-2-ethyl-5-hydroxy-phenoxy]-2-hydroxy-propoxy)-4-benzyloxy-coumarin | 195 | 37 | Found; C, 68.98; H, 5.67; $C_{29}H_{28}O_8$ |
| 60 | 7-(3-[2-Allyl-3-hydroxy-4-propionyl-phenoxy]-2-hydroxy-propoxy)-4-benzyloxy-coumarin | 117 | 25 | Found; C, 70.19; H, 5.54; $C_{31}H_{30}O_8$ requires; C, 70.17; H, 5.70 |
| 61 | 7-(3-[4-Acetyl-3-hydroxy-2-n-propyl-phenoxy]-2-hydroxy-propoxy)-8-methyl-4-benzyloxycoumarin | 201–203 | 37 | Found; C, 68.83; H, 6.04; $C_{31}H_{33}O_8 \cdot 0.5H_2O$ requires; C, 68.61; H, 6.31 |
| 62 | 7-(3-[4-Acetyl-3-hydroxy-2-n-prop phenoxy]-2- | foam | 41 | R$_f$(CHCl$_3$/SiO$_2$) 0.50 |

TABLE IV-continued

| Example | Compound | m.p. °C | Yield % | Analysis |
|---|---|---|---|---|
| | hydroxypropoxy)-8-allyl-4-benzyloxycoumarin | | | |
| 63 | 7-(3-[4-Acetyl-3-hydroxy-2-n-propylphenoxy]-2-hydroxypropoxy)-8-n-propyl-4-benzyloxy-coumarin | foam | 38 | $R_f$ (CHCl$_3$/SiO$_2$) 0.43 |
| 64 | 4-Benzyloxy-7-(2 hydroxy-3-[4-fluoro-2-n-propyl-phenoxy]propoxy)coumarin | m.p. 124–126 | 41 | Found; C, 70.08; H, 5.76; $C_{28}H_{27}FO_6$ requires; C, 70.28; H, 5.69 |

EXAMPLE 65

4-Hydroxy-7-(3-phenoxypropoxy) coumarin

A solution of 2-hydroxy-4-(3-phenoxypropoxy) acetophenone (14.55 g; 0.0509 mole) in dry benzene (100 ml) was added to a stirred, refluxing suspension of 60% sodium hydride in mineral oil (4.60 g; 0.115 mole) in dry benzene (100 ml) over 30 minutes. After a further 10 minutes a solution of diethyl carbonate (12.02 g; 0.102 mole) in dry benzene (100 ml) was added over 1 hour at reflux and the solution maintained at reflux for a further 19 hours. After cooling, the mixture was poured on to iced 2 N hydrochloric acid (550 ml) and the precipitated solid filtered off and washed well with water. Recrystallisation from ethanol in the presence of charcoal gave 10.35 g (65%) of the title compound as a white solid of m.p. 190°–192° C. (dec); $\nu$max (mull) 3270, 2600 (br), 1715, 1650, 1610 cm$^{-1}$; $\tau$(DMSO), 7.74 (2H, quintet, J 6.5 Hz), 5.80 (2H, t, J 5.5 Hz); 5.68 (2H, t, J 7.0 Hz); 4.38 (1H, s); 3.17–2.48 (7H, m); 2.20 (1H, d, J 9.0 Hz); 1 low field exchangeable proton. (Found; C, 69.22; H, 5.21; $C_{18}H_{16}O_5$ requires; C, 69.22; H, 5.16%).

The compounds listed in Table V were prepared in an analogous manner.

TABLE V

| Example | Compound | m.p. °C | Yield % | Analysis |
|---|---|---|---|---|
| 66 | 4-Hydroxy-6-(2-phenyl-ethoxy) coumarin | 189 | 71 | Found; C, 71.95; H, 4.95; $C_{17}H_{14}O_4$ requires; C, 72.33; H, 5.00 |
| 67 | 4-Hydroxy-7-(2-phenyl-ethoxy) coumarin | 203 | 49 | Found; C, 72.34; H, 4.98; $C_{17}H_{14}O_4$ requires; C, 72.33; H, 5.00 |
| 68 | 4-Hydroxy-6-(3-phenyl-propoxy) coumarin | 212 | 83 | Found; C, 73.02; H, 5.62; $C_{18}H_{16}O_4$ requires; C, 72.96; H, 5.44 |
| 69 | 4-Hydroxy-7-(3-phenyl-propoxy) coumarin | 255 | 56 | Found; C, 72.77; H, 5.70; $C_{18}H_{16}O_4$ requires; C, 72.96; H, 5.44 |
| 70 | 4-Hydroxy-7-(4-phenyl-butoxy) coumarin | 192 | 42 | Found; C, 73.53; H, 5.98 |
| 71 | 7-4-[4-Chlorophenyl]butoxy)-4-hydroxy coumarin | 209–210.5 | 63 | Found; C, 66.05; H, 4.95; Cl, 10.46; $C_{19}H_{17}ClO_4$ requires; C, 66.19; H, 4.97; Cl, 10.28 |
| 72 | 4-Hydroxy-7-(4-[4-methylphenyl]butoxy) coumarin | 198–201 | 57 | Found; C, 73.80; H, 6.14; $C_{20}H_{20}O_4$ requires; C, 74.07; H, 6.17 |
| 73 | 4-Hydroxy-6-(2-phenoxyethoxy)-coumarin | 211 | 39 | Found; C, 68.67; H, 4.79; $C_{17}H_{14}O_5$ requires; C, 68.45; H, 4.73 |
| 74 | 4-Hydroxy-7-(2-phenoxy-ethoxy) coumarin | 244 | 39 | Found; C, 68.50; H, 4.84; $C_{17}H_{14}O_5$ requires; C, 68.45; H, 4.73 |
| 75 | 4-Hydroxy-6-(3-phenoxy-propoxy) coumarin | 204–205 | 71 | Found; C, 69.18; H, 5.35; $C_{18}H_{16}O_5$ requires; C, 69.22; H, 5.16 |
| 76 | 4-Hydroxy-7-(4-phenoxy-butoxy) coumarin | 194 | 70 | Found; C, 69.92; H, 5.61; $C_{19}H_{18}O_5$ requires; C, 69.93; H, 5.56 |
| 77 | 4-Hydroxy-6-(5-phenoxy-pentoxy) coumarin | 163–164 | 40 | Found; C, 66.61; H, 5.83; $C_{20}H_{20}O_5H_2O$ requires; C, 67.03; H, 6.19 |
| 78 | 4-Hydroxy-7-(5-phenoxy-pentoxy) coumarin | 180 | 49 | Found; C, 70.54; H, 6.00; $C_{20}H_{20}O_5$ |
| 79 | 4-Hydroxy-6-(6-phenoxy-hexoxy) coumarin | 162–163 | 58 | Found; C, 70.37; H, 6.47; $C_{21}H_{22}O_5$ requires; C, 71.17; H, 6.26 |
| 80 | 4-Hydroxy-7-(6-phenoxy-exoxy) coumarin | 170 | 22 | Found; C, 69.36; H, 6.12; $C_{21}H_{22}O_5 0.5H_2O$ requires; C, 69.41; H, 6.38 |
| 81 | 7-(3-[4-Chlorophenoxy] | 230–234 | 71 | Found; C, 62.00; H, 4.76; Cl, |

TABLE V-continued

| Example | Compound | m.p. °C. | Yield % | Analysis |
|---|---|---|---|---|
| | propoxy)-4-hydroxy-coumarin | | | 10.22; $C_{18}H_{15}ClO_5$ requires; C, 62.35; H, 4.36; Cl, 10.22 |
| 82 | 4-Hydroxy-7-(3-[4-methylphenoxy]propoxy) coumarin | 209–212 | 69 | Found; C, 69.99; H, 5.86; $C_{19}H_{18}O_5$ requires; C, 69.93; H, 5.56 |
| 83 | 4-Hydroxy-7-(3-[3-methylphenoxy]propoxy) coumarin | 192 | 26 | Found: C, 69.75; H, 5.62; $C_{19}H_{18}O_5$ requires; C, 69.93; H, 5.56 |
| 84 | 4-Hydroxy-7-(3-[2-methylphenoxy]propoxy) coumarin | 203 | 24 | Found; C, 69.82; H, 5.80; $C_{19}H_{18}O_5$ requires; C, 69.93; H, 5.56 |
| 85 | 4-Hydroxy-7-(3-[4-methoxyphenoxy]coumarin | 193–196 | | Found; C, 66.66; H, 5.52 $C_{19}H_{18}O_6$ requires; C, 66.66; H, 5.30 |
| 86 | 7-(3-[4-Fluorophenoxy]propoxy)-4-hydroxy-coumarin | 203–206 | 58 | Found; C, 65.67; H, 4.84; $C_{18}H_{15}FO_5$ requires; C, 65.45; H, 4.55 |
| 87 | 7-(3-[4-Cyanophenoxy]propoxy)-4-hydroxy-coumarin | 180–184 | 50 | Found; C, 67.81; H, 5.03; N, 3.92; $C_{19}H_{15}NO_5$ requires; C, 67.66; H, 4.45; N, 4.15 |
| 88 | 4-Hydroxy-7-(3-[4-phenylphenoxy]propoxy) coumarin | 240–242 | 76 | Found; C, 74.10; H, 5.32; $C_{24}H_{20}O_5$ requires; C, 74.23; H, 5.15 |
| 89 | 4-Hydroxy-7-(3-[5,6,7,8-tetranhydro-2-naphthyloxy]coumarin | 199–201 | 42 | Found; C, 72.12; H, 6.07; $C_{22}H_{22}O_5$ requires; C, 72.13; H, 6.01 |
| 90 | 6-Ethyl-4-hydroxy-7-(3-phenoxypropoxy)coumarin | 233–234 | 73 | Found; C, 70.29; H, 6.12; $C_{20}H_{20}O_5$ requires; C, 70.58; H, 5.92 |
| 91 | 4-Hydroxy-7-(3-phenoxy-propoxy)-8-n-propyl coumarin | 149–150 | 95 | Found; C, 70.88; H, 6.56; $C_{21}H_{22}O_5$ requires; C, 71.77; H, 6.26 |

EXAMPLE 92

4-Hydroxy-7-(2-hydroxy-3-phenoxypropoxy) coumarin

A solution of 3,4-dihydro-7-(2-hydroxy-3-phenoxy-propoxy)-4-iminocoumarin (6.5 g; 0.02 mole) in 50% w/v sulphuric acid (80 g) was stirred at 100° for 3–6 hours. The initial pale red solution precipitated a yellow solid which after cooling and dilution with water was separated by decantation. After several decantations with water the oily solid was taken up in hot ethanol, charcoaled, filtered and the filtrate gradually diluted with water. The precipitated oily solid crystallised overnight to give 2.934 of buff solid of m.p. 145°–175°. Recrystallisation from aqueous methanol gave 2.275 g (34%) of material of m.p. 181°–183°, νmax (mull) 3250, 3060, 1705, 1610 cm$^{-1}$; τ(DMSO); 5.85 (5H, m); 4.75 (1H broad exchangeable); 4.50 (1H, sharp exchangeable singlet); 3.19–2.50 (7H, complex m); 2.22 (1H, d, J 9.0 Hz); 1 low field exchangeable singlet. (Found; C, 65.48; H, 5.19; $C_{18}H_{16}O_6$ requires; C, 65.85; H, 4.91%)

Similarly were prepared the compounds in Table VI.

TABLE VI

| Example | Compound | m.p. °C. | Yield % | Analysis |
|---|---|---|---|---|
| 93 | 7-(3-[4-Acetyl-3-hydroxyphenoxy]propoxy)-4-hydroxycoumarin | 220–222 | 71 | Found; C, 65.02; H, 5.08; $C_{20}H_{18}O_7$ requires; C, 64.86; H, 4.90 |
| 94 | 7-(3-[4-Acetylphenoxy]propoxy)-4-hydroxycoumarin | 202–204 | 55 | Found; C, 67.39; H, 5.26; $C_{20}H_{18}O_6$ requires; C, 67.79; H, 5.12 |
| 95 | 4-hydroxy-5-methyl-7-(3-phenoxypropoxy)coumarin | 218–219 | 65 | Found; C, 70.31; H, 5.43; $C_{19}H_{18}O_5$ requires; C, 69.93; H, 5.56 |
| 96 | 7-(3-[4-Carboxyphenoxy]propoxy)-4-hydroxycoumarin | 275–276 | 80 | |
| 97 | 7-(3-[Carboxyphenoxy]-2-2-hydroxy-propoxy)-4-hydroxycoumarin | 169–172 (foams) | 95 | |

EXAMPLE 98

7-(3-[4-Acetyl-3-hydroxy-2-n-propylphenoxy]-2-hydroxypropoxy)-4-hydroxycoumarin

Hydrogenation of 7-(3-[4-acetyl-3-hydroxy-2-n-propylphenoxy]-2-hydroxypropoxy)-4-benzyloxycoumarin (3.42 g; 0.0066 mole) in DMF (60 ml) at atmospheric pressure using 10% palladinized charcoal afforded the title compound; 2.86 g as a tlc pure foam. (DMSO); 9.13 (3H, t, J 6.7 Hz); 8.59 (2H, m) 7.40 (3H, s); 7.40 (2H, m); 6.30 (1H, broad exchangeable); 5.75 (5H, s); 4.75 (1H, broad exchangeable); 4.50 (1H, exchangeable) 3.30 (1H, d, J 9.3 Hz); 3.01 (2H, m); 2.23

(1H, d, J 9.6 Hz); 2.15 (1H, d, J 9.3 Hz); 1 low field sharp exchangeable. Molecular ion at m/e 428.

By a similar procedure the examples in Table VII were prepared.

from ethanol to give 2.42 g, (78%) of yellow solid of mp 201°–203° (dec). νmax (mull) 3350 (br), 1770, 1620, 1610, 1540 cm$^{-1}$; τ(DMSO); 9.17 (3H, t, J 6.9 Hz); 8.55 (2H, m, J ca 7 Hz); 7.43 (3H, S+2H, m); 5.78 (5H, S);

TABLE VII

| Example | Compound | m.p. °C. | Yield % | Analysis |
|---|---|---|---|---|
| 99 | 7-(2-[4-Fluorophenyl]ethoxy)-4-hydroxycoumarin | 218 | 50 | Found; C, 67.46; H, 4.53; $C_{17}H_{13}FO_4$ requires; C, 68.00; H, 4.36 |
| 100 | 7-(3-[4-Acetylphenyl]propoxy)-4-hydroxycoumarin | 205 | 75 | Found; C, 71.25; H, 5.66; $C_{20}H_{18}O_5$ requires; C, 70.99; H, 5.36 |
| 101 | 7-(3-[4-Chlorophenoxymethoxy])-4-hydroxycoumarin | 218 | 95 | Found; C, 60.63; H, 3.76; Cl, 11.17; $C_{16}H_{11}ClO_5$ requires; C, 60.24; H, 3.48; Cl, 11.13 |
| 102 | 7-(2-[4-Acetyl-3-hydroxy-2-n-propulphenoxy]ethoxy)-4-hydroxy-coumarin | 211–216 | 81 | Found; C, 66.48; H, 5.80; $C_{22}H_{22}O_7$ requires; C, 66.32; H, 5.57 |
| 103 | 7-(3-[4-Carbomethoxyphenoxy]propoxy)-4-hydroxycoumarin | 218 | 83 | Found; C, 64.51; H, 5.08; $C_{20}H_{18}O_7$ requires; C, 64.86; H, 4.90 |
| 104 | 4-Hydroxy-7-(2-hydroxy-3-[2-n-propylphenoxy]propoxy) coumarin | 197 | 89 | Found; C, 66.87; H, 5.86; $C_{21}H_{20}O_6 \cdot 0.5H_2O$ requires; C, 66.48; H, 6.11 |
| 105 | 7-(3-[4-Acetyl-3-hydroxyphenoxy]-2-hydroxypropoxy)-4-hydroxycoumarin | ca205 | 60 | |
| 106 | 7-(3-[4-Acetyl-2-n-propylphenoxy]-2-hydroxypropoxy)-4-hydroxycoumarin | | | |
| 107 | 7-(3-[4-Acetyl-3-hydroxy-2-methyl-phenoxy]-2-hydroxypropoxy)-4-hydroxycoumarin | 230 | 64 | Found; C, 62.78; H, 5.23; $C_{21}H_{20}O_8$ requires; C, 62.99; H, 5.04 |
| 108 | 7-(3-[4-Acetyl-2-ethyl-5-hydroxy-phenoxy]-2-hydroxypropoxy)-4-hydroxycoumarin | 240 | 87 | Found; C, 63.47; H, 5.50; $C_{22}H_{22}O_8$ requires; C, 63.76; H, 5.35 |
| 109 | 4-Hydroxy-7-(3-[3-hydroxy-4-propionyl-2-n-propylphenoxy]-2-hydroxypropoxy) coumarin | 89 | 61 | Found; C, 65.22; H, 6.26; $C_{24}H_{26}O_8$ requires; C, 65.10; H, 5.92 |
| 110 | 7-(3-[4-Acetyl-3-hydroxy-2-n-propylphenoxy]-2-hydroxypropoxy)-4-hydroxy-8-methyl coumarin | 118–120 | 93 | Found; C, 62.47; H, 6.16; $C_{24}H_{26}O_8 \cdot H_2O$ requires; C, 62.60; H, 6.13 |
| 111 | 7-(3-[4-Acetyl-3-hydroxy-2-n-propylphenoxy]-2-hydroxypropoxy)-4-hydroxy-8-n-propylcoumarin | foam | 100 | |
| 112 | 7-(3-[4-Acetyl-3-hydroxy-2-n-propylphenoxyl]propoxy)4-hydroxycoumarin | 166 | 70 | Found; C, 66.74; H, 6.03; $C_{23}H_{24}O_7$ requires; C, 66.98; H, 5.86 |
| 113 | 7-(3-[4-Fluoro-2-n-propylphenoxy]-2-hydroxypropoxy)-4-hydroxy coumarin | m.p.195 | 95 | Found; C, 65.24; H, 5.77; $C_{21}H_{21}FO_6$ requires; C, 64.94; H, 5.45. |

EXAMPLE 114

7-(3-[4-Acetyl-3-hydroxy-2-n-propylphenoxy]-2-hydroxypropoxy)-4-hydroxy-3-nitrocoumarin

Fuming nitric acid (9 ml) was added to a stirred suspension of 7-(3-[4-Acetyl-3-hydroxy-2-n-propylphenoxy]-2-hydroxypropoxy)-4-hydroxycoumarin (2.8 g) in chloroform (300 ml) over 1 hr at 0° and the dark mixture stirred for a further 0.5 hr at this temperature. Dilute hydrochloric acid (150 ml) was added and the chloroform removed in vacuo at 0°. The solid which separated was removed by filtration and recrystallised 3.20 (3H, m); 2.16 (2H, exchangeable S); 2.16 (2H, near doublet); 1 low field broad exchangeable). (Found, C, 58.49; H, 5.07; N, 3.04; $C_{23}H_{23}NO_{10}$ requires, C, 58.35; H, 4.90; N, 2.96%).

The sodium salts, prepared in the usual manner, had mp 262° (dec); νmax (mull) 1720, 1620, 1605 cm$^{-1}$ (Found; C, 56.01; H, 4.77; N, 2.80; Na 4.73; $C_{23}H_{22}NNaO_{10}$; requires; C, 55.76; H, 4.48; N, 2.83; Na, 4.64%)

By a similar procedure the examples listed in Table VIII were prepared.

TABLE VIII

| Example | Compound | m.p. °C. | Yield % | Analysis |
|---|---|---|---|---|
| 115 | 4-Hydroxy-3-nitro-6-(2-phenylethoxy) coumarin | 166 | 73 | Found; C, 62.09; H, 3.86; N, 4.35; $C_{17}H_{13}NO_6$ requires; C, 62.39; H, 4.00; N, 4.28; Sodium Salt m.p. 230° |
| 116 | 4-Hydroxy-3-nitro-7-(2-phenylethoxy) coumarin | 154 | 83 | Found; C, 62.39; H, 4.12; N, 4.28; $C_{17}H_{13}NO_6$ requires; C, 62.39; H, 4.00; N, 4.28 |
| 117 | 7-(2-[4-Fluorophenyl]ethoxy)-4-hydroxy-3-nitrocoumarin | 162 | 95 | Found; C, 58.92; H, 3.69; N, 4.25; $C_{17}H_{12}FNO_6$ requires; C, 59.13; H, 3.50; N, 4.06 |
| 118 | 4-Hydroxy-3-nitro-6-(3-phenylpropoxy) coumarin | 137–138 | 79 | Found; C, 63.38; H, 4.51; N, 4.17; $C_{18}H_{15}NO_6$ requires; C, 63.34; H, 4.43; N, 4.10; Sodium Salt; m.p. 226°–227° |

TABLE VIII-continued

| Example | Compound | m.p. °C. | Yield % | Analysis |
|---|---|---|---|---|
| 119 | 4-Hydroxy-3-nitro-7-(3-phenylpropoxy) coumarin | 192–195 | 73 | Found; C, 63.34; H, 4.57; N, 4.31; $C_{18}H_{15}NO_6$ requires; C, 63.34; H, 4.43; N, 4.10 |
| 120 | 7-(3-[4-Acetylphenyl]propoxy)-4-hydroxy-3-nitrocoumarin | 135 | 70 | Found; C, 62.36;;H, 4.66; N, 3.52; $C_{20}H_{17}NO_7$ requires; C, 62.66; H, 4.47; N, 3.65; Sodium Salt; m.p. 200° |
| 121 | 4-Hydroxy-3-nitro-7-(4-phenylbutoxy) coumarin | 132 | 88 | Found; C, 63.98; H, 4.89; N, 4.03; $C_{19}H_{17}NO_6$ requires; C, 63.72; H, 4.82; N, 3.94 |
| 122 | 7-(4-[4-Chlorophenyl]butoxy)-4-hydroxy-3-nitrocoumarin | 157–160 | 62 | Found; C, 58.81; H, 4.16; N, 3.91; Cl, 9.00; $C_{19}H_{16}ClNO_6$ requires; C, 58.54; H, 4.14; N, 3.59; Cl, 9.10 |
| 123 | 4-Hydroxy-7-(4-[4-methylphenyl]butoxy)-3-nitrocoumarin | 145–147 | 88 | Found; C, 64.52; H, 5.09; N, 3.73; $C_{20}H_{19}NO_6$ requires; C, 65.04; H, 5.15; N, 3.79 |
| 124 | 7-(4-Chlorophenoxymethoxy)-4-hydroxy-3-nitrocoumarin | 130 | 70 | Found; C, 52.92; H, 2.69; N, 3.86; Cl, 9.97; $C_{16}H_{10}ClNO_7$ requires; C, 52.83; H, 2.77; N, 3.85; Cl, 9.75 Sodium Salt; m.p. 229°–230° |
| 125 | 4-Hydroxy-3-nitro-6-(2-phenoxyethoxy) coumarin | 164–165 | 45 | Found; C, 59.57; H, 3.80; N, 3.86; $C_{17}H_{13}NO_7$ requires; C, 59.48; H, 3.81; N, 4.08 |
| 126 | 4-Hydroxy-3-nitro-7-(2-phenoxyethoxy) coumarin | 188 | 69 | Found; C, 59.70; H, 4.14; N, 3.72; $C_{17}H_{13}NO_7$ requires; C, 59.48; H, 3.81; N, 4.08 |
| 127 | 7-(2-[4-Acetyl-3-hydroxy-2-n-propylphenoxy]ethoxy)-4-hydroxy-3-nitrocoumarin | | | |
| 128 | 4-Hydroxy-3-nitro-6-(3-phenoxypropoxy) coumarin | 138–140 | 43 | Found; C, 60.57; H, 4.31; N, 3.65; $C_{18}H_{15}NO_7$ requires; C, 60.51; H, 4.23; N, 3.92 |
| 129 | 4-Hydroxy-3-nitro-7-(3-phenoxypropoxy) coumarin | 148–150 | 82 | Found; C, 60.39; H, 4.12; N, 4.01; $C_{18}H_{15}NO_7$ requires; C, 60.51; H, 4.23; N, 3.92; D-N-methylglucamine salt; m.p. 130°–132° Found; C, 54.19; H, 5.80; N 4.82; $C_{25}H_{32}NO_{12}$ requires; C, 54.34; H, 5.84; N, 5.07 |
| 130 | 4-Hydroxy-5-methyl-3-nitro-7-(3-phenoxypropoxy) | 134–137 | 67 | Found; C, 61.49; H, 4.62; N, 4.11; $C_{19}H_{17}NO_7$ requires; C, 61.45; H, 4.61; N, 3.77; Sodium Salt; m.p. 223°–225° |
| 131 | 4-Hydroxy-3-nitro-7-(3-phenoxy-propoxy) 8-n-propylcoumarin | 136–137 | 84 | Found; C, 63.35; H, 5.54; N, 3.54; $C_{21}H_{21}NO_7$ requires; C, 63.15; H, 5.30; N, 3.51; Sodium Salt; m.p. 186° Found; C, 59.88; H, 4.85; N, 2.99; Na 5.90; $C_{21}H_{20}NNaO_7$ requires; C, 59.86; H, 4.78; N, 3.32; Na, 5.46 |
| 132 | 6-Ethyl-4-hydroxy-3-nitro-7-(3-phenoxypropoxy) coumarin | 154–155 | 88 | Found; C, 62.02; H, 5.08; N, 3.77; $C_{20}H_{19}NO_7$ requires; C, 62.33; H, 4.97; N, 3.63; Sodium Salt; m.p. 257°–258° |
| 133 | 7-(3-[4-Chlorophenoxy]propoxy)-4-hydroxy-3-nitrocoumarin | 139–145 | 72 | Found; C, 55.18; H, 3.53; N, 3.55; Cl, 9.20; $C_{18}H_{14}ClNO_7$ |
| 134 | 7-(3-[4-Carboxyphenoxy]propoxy)-4-hydroxy-3-nitrocoumarin | 239–240 | 55 | Found; C, 57.61; H, 4.08; N, 3.27; $C_{19}H_{15}NO_9$ |
| 135 | 7-(3-[4-Carbomethoxyphenoxy]propoxy)-4-hydroxy-3-nitrocoumarin | 164–168 | 87 | Found; C, 57.80; H, 4.11; N, 3.41; $C_{20}H_{17}NO_9$ requires; C, 57.83; H, 4.13; N, 3.37; Sodium Salt; m.p. 255°–257° |
| 136 | 7-(3-[4-Acetylphenoxy]propoxy)-4-hydroxy-3-nitrocoumarin | 159–161 | 52 | Found; C, 60.44; H, 4.67; N, 3.36; $C_{20}H_{17}NO_8$ requires; C, 60.15; H, 4.29; N, 3.51 |
| 137 | 4-Hydroxy-7-[4-methyl-2-nitrophenoxy]propoxy)- | 183–185 | 20 | Found; C, 54.97; H, 4.18; N, 6.78; $C_{19}H_{16}N_2O_9$ |

TABLE VIII-continued

| Example | Compound | m.p. °C | Yield % | Analysis |
|---|---|---|---|---|
| | 3-nitrocoumarin | | | requires; C, 54.81; H, 3.87; N, 6.73 |
| 138 | 7-(3-[4-Acetyl-3-hydroxyphenoxy]propoxy)-4-hydroxy-3-nitrocoumarin | 199–200 | 75 | Found; C, 57.55; H, 4.28; N, 3.67; $C_{20}H_{17}NO_9$ requires; C, 57.83; H, 4.13; N, 3.37; Sodium Salt, m.p. 265°–267° |
| 139 | 7-(3-[4-Acetyl-3-hydroxy-2-n-propylphenoxy]propoxy)-4-hydroxy-3-nitrocoumarin | 148 | 74 | Found; C, 60.36; H, 5.13; N, 2.87; $C_{23}H_{23}NO_9$ requires; C, 60.39; H, 5.07; N, 3.06; Sodium Salt; m.p. 254° |
| 140 | 7-(3-[4-Carboxyphenoxy]-2-hydroxy-propyoxy)-4-hydroxy-3-nitrocoumarin | 220–221 | 49 | Found; C, 54.34; H, 3.87; N, 3.68; $C_{19}H_{15}NO_{10}$ requires; C, 54.68; H, 3.62; N, 3.36 |
| 141 | 4-Hydroxy-7-(2-hydroxy-3-phenoxypropoxy)-3-nitrocoumarin | 179–180 | 50 | Found; C, 57.89; H, 4.05; N, 3.85; $C_{18}H_{15}NO_8$ requires; C, 57.91; H, 4.05; N, 3.75 |
| 142 | 7-(3-[4-Acetyl-2-n-propylphenoxy]-2-hydroxypropoxy)-4-hydroxy-3-nitrocoumarin | | | |
| 143 | 7-(3-[4-Acetyl-3-hydroxyphenoxy]2-hydroxypropoxy)-4 hydroxy-3-nitro-coumarin | 120 | 49 | Found; C, 54.74; H, 4.15; N, 3.31; $C_{20}H_{17}NO_{10} \cdot 0.5H_2O$ Requires; C, 54.54; H, 4.12; N, 3.18 Sodium salt; m.p. 235° (dec) |
| 144 | 7-(3-[4-Acetyl-3-hydroxy-2-methyl-phenoxy]-2-hydroxypropoxy)-4-hydroxy-3-nitrocoumarin | 204 | 67 | Found; C, 55.49; H, 4.64; N, 2.94; $C_{21}H_{19}NO_{10} \cdot 0.5H_2O$ requires; C, 55.50; H, 4.43; N, 3.08 Sodium salt; m.p. 185° (dec) |
| 145 | 7-(3-[4-Acetyl-2-ethyl-5-hydroxy-phenoxy]-2-hydroxy-propoxy)-4-hydroxy-3-nitrocoumarin | 150 | 30 | Found; C, 56.36; H, 4.66; N, 2.99; $C_{22}H_{21}NO_{10} \cdot 0.5H_2O$ requires; C, 56.41; H, 4.73; N, 2.99 |
| 146 | 6-(3-[4-Acetyl-3-hydroxy-2-n-propyl-phenoxy]-2-hydroxy-propoxy)-4-hydroxy-3-nitrocoumarin | | | |
| 147 | 7-(3-[4-Acetyl-3-hydroxy-2-n-propyl-phenoxy]-2-hydroxy-propoxy)-4-hydroxy-8-methyl-3-nitro-coumarin | | | |
| 148 | 7-(3-[4-Acetyl-3-hydroxy-2-n-propyl-phenoxy]-2-hydroxy-propoxy)-4-hydroxy-3-nitro-8-n-propyl-coumarin | foam | 98 | Found; C, 59.00; H, 5.42; N, 2.61 $C_{26}H_{29}NO_{10} \cdot 0.75H_2O$ requires; C, 59.03; H, 5.81; N, 2.65 Sodium Salt; foam Found; C, 57.21; H, 5.61; N, 2.55; Na, 4.68; $C_{26}H_{28}NNaO_{10}.05H_2O$ Requires; C, 57.14; H, 5.35; N, 2.56; Na, 4.21 |
| 149 | 4-Hydroxy-7-(2-hydroxy-3-[3-hydroxy-4-propionyl-2-n-propylphenoxy]pro-poxy)-3-nitrocoumarin | 74 | 83 | |
| 150 | 4-Hydroxy-3-nitro-7-(4-phenoxybutoxy)-coumarin | 152–154 | 96 | Found; C, 61.45; H, 4.69; N, 3.59; $C_{19}H_{17}NO_7$ requires; C, 61.45; H, 4.45; N, 4.61 Sodium salt; m.p. 195° Found; C, 55.80; H, 4.01; N, 3.33; $C_{19}H_{16}NNaO_7$ requires; C, 55.47; H, 4.38; N, 3.41; Na, 5.60 |
| 151 | 4-Hydroxy-3-nitro-6-(5-phenoxypentoxy)-coumarin | 110 | 20 | Sodium Salt; m.p. 192° |
| 152 | 4-Hydroxy-3-nitro-7-(5-phenoxypentoxy)-coumarin | 143–145 | 77 | Found; C, 62.02; H, 5.02; N, 3.43; $C_{20}H_{19}NO_7$ requires; C, 62.33; H, 4.87; N, 3.62 |
| 153 | 4-Hydroxy-3-nitro-6-(6-phenoxyhexoxy)coumarin | 90–91 | 37 | Found; C, 62.61; H, 5.45; N, 3.65 $C_{21}H_{21}NO_7$ requires; C, 63.15; H, 5.30; N, 3.51 |
| 154 | 4-Hydroxy-3-nitro-7- | 110 | 66 | Found; C, 63.18; H, 5.41; N, 3.27; |

TABLE VIII-continued

| Example | Compound | m.p. °C. | Yield % | Analysis |
|---|---|---|---|---|
| | (6-phenoxyhexoxy) coumarin | | | $C_{21}H_{21}NO_7$ requires; C, 63.15; H, 5.30; N, 3.51 |

EXAMPLE 155

4-Hydroxy-7-(3-[2-methylphenoxy]propoxy)-3-nitrocoumarin

Sodium nitrite (0.24 g; 0.003 mole) was added in one portion to a vigorously stirred suspension of 4-hydroxy-7-(3-[2-methylphenoxy] propoxy) coumarin (1 g) in glacial acetic acid (30 ml). After 2 hrs. at ambient temperature the reddish solution was poured into water (150 ml) and the precipitated yellow solid filtered off. Recrystallisation from aqueous ethanol gave 0.815 g (70%) of yellow 3-nitro derivative of m.p. 146°; $\nu$max (mull) 1750, 1615, 1600, 1525 cm$^-$; $\tau$(DMSO); 7.85 (3H, S); 7.82 (2H, quintet); 5.88 (2H, t, J 7.2 Hz); 5.72 (2H, t, J 7.2 Hz); 3.23–2.73 (6H, m); 2.13 (1H, d, J 9.3 Hz); 1 sharp low field exchangeable proton. (Found; C, 61.25; H, 4.56; N, 3.58; $C_{19}H_{17}NO_7$ requires; C, 61.45; H, 4.61; N, 3.77%).

The sodium salt has m.p. 225°. (Found: C, 57.80; H, 4.38; N, 3.38; Na, 5.96; $C_{19}H_{16}NNaO_7$ requires; C, 58.02; H, 4.10; N, 3.56; Na, 5.86%).

By a similar procedure may be made the compounds of Table IX.

EXAMPLE 165

7-[2-(4-Acetyl-3-hydroxy-6-nitro-2-n-propylphenoxy)ethoxy]-4-hydroxy-3-nitrocoumarin Fuming nitric acid (9 ml; d 1.52) was added dropwise over 1 hour to a stirred suspension of 7-[2(4-acetyl-3-hydroxy-2-n-propylphenoxy)ethoxy]-4-hydroxycoumarin (1.4 g) in chloroform (200 ml) at 0° and left at this temperature for a further 1 hour. Evaporation of the solvent in vacuo afforded a dark oil which precipitated an orange solid on dilution with dilute hydrochloric acid. Repeated recrystallisation of this solid from ethanol-DMF gave 0.39 g of the title compound of mp 180°–181° (dec). (Found; C, 54.42; H, 4.39; N, 6.08; $C_{22}H_{20}N_2O_{11}$ requires; C, 54.10; H, 4.13; N, 5.74%).

EXAMPLE 166

7-[3-(4-Acetyl-3-hydroxy-6-nitro-2-n-propylphenoxy)-2-hydroxy-propoxy]-4-hydroxy-8-methyl-3-nitrocoumarin Nitration of a suspension of 7-[3-(4-acetyl-3-hydroxy-2-n-propylphenoxy)-2-hydroxypropoxy]-4-hydroxy-8-methylcoumarin (1.5 g) in chlorofrom (200 ml) as de-

TABLE IX

| Example | Compound | m.p. °C. | Yield % | Analysis |
|---|---|---|---|---|
| 156 | 4-Hydroxy-7-(3-[3-methylphenoxy]propoxy)-3-nitrocoumarin | 142 | 64 | Found; C, 61.12; H, 4.50; N, 3.67 $C_{19}H_{17}NO_7$ requires; C, 61.45; H, 4.61; N, 3.77 Sodium salt; m.p. 210° Found; C, 55.50; H, 4.59; N, 3.55; $C_{19}H_{16}NNaO_7$ requires; C, 55.48; H, 4.41; N, 3.41 |
| 157 | 4-Hydroxy-7-(3-[4-methylphenoxy]propoxy)-3-nitrocoumarin | 170–172 | 21 | Found; C, 61.83; H, 4.76; N, 3.62; $C_{19}H_{17}NO_7$ requires; C, 61.45; H, 4.61; N, 3.77 |
| 158 | 4-Hydroxy-7-(3-[4-methoxyphenoxy]propoxy)-3-nitrocoumarin | 167–175 | 52 | Found; C, 59.21; H, 4.82; N, 3.36; $C_{19}H_{17}NO_8$ requires; C, 58.91; H, 4.42; N, 3.62 |
| 159 | 7-(3-[4-Fluorophenoxy]propoxy)-4-hydroxy-3-nitrocoumarin | 173–176 | 24 | Found; C, 57.49; H, 4.10; N, 3.57; $C_{18}H_{14}FNO_7$ requires; C, 57.60; H, 3.73; N, 3.73 |
| 160 | 7-(3[4-Cyanophenoxy]propoxy)-4-hydroxy-3-nitrocoumarin | 204 | 40 | Found; C, 59.43; H, 3.92; N, 7.04; $C_{19}H_{14}FNO_7$ requires; C, 59.69; H, 3.66; N, 7.33 |
| 161 | 4-Hydroxy-7-(3-[4-phenylphenoxy]propoxy)-3-nitrocoumarin | | | Found; C, 66.40; H, 4.60; N, 3.14; $C_{24}H_{19}NO_7$ requires; C, 66.51; H, 4.42; N, 3.23 |
| 162 | 4-Hydroxy-3-nitro-7-(3-[5,6,7,8-tetrahydro-2-naphthyloxy]propoxy) coumarin | 127–134 | 40 | Found; C, 63.85; H, 5.44; N, 3.10; $C_{22}H_{21}NO_7$ requires; C, 64.23; H, 5.11; N, 3.41 |
| 163 | 4-Hydroxy-7-(2-hydroxy-3-[2-n-propylphenoxy]propoxy)-3-nitrocoumarin | 125–126 | 87 | Found; C, 60.43; H, 5.18; N, 3.62; $C_{21}H_{21}NO_8$ requires; C, 60.72; H, 5.10; N, 3.37 |
| 164 | 7-(3-[4-Fluoro-2-hydroxypropoxy)-4-hydroxy-3-nitrocoumarin | m.p. 136–138 | 92 | Found; C, 56.28; H, 4.62; N, 3.60; $C_{21}H_{20}FNO_8$ requires; C, 55.88; H, 4.91; N, 3.10 | scribed above afforded 0.35 g of dinitro derivative of mp 127° after repeated recrystallisation from ethanol. (Found; C, 53.44; H, 4.78; N, 5.15; $C_{24}H_{24}N_2O_{12}$, $0.5H_2O$ requires; C, 53.24; H, 4.65; N, 5.17%).

C, 64.55; H, 5.36; $C_{17}H_{16}O_6$ requires; C, 64.55; H, 5.10%).

The compounds listed in Table XI were similarly prepared.

TABLE XI

| EXAMPLE | COMPOUND | m.p. °C. | YIELD % | ANALYSIS |
|---|---|---|---|---|
| 171 | 4-(3-Phenylpropoxy) phthalic acid | 158–161 | 100 | Found; C, 68.00; H, 5.52; $C_{17}H_{16}O_5$ Requires; C, 67.99; H, 5.37% |
| 172 | 4-[3-(2,3,5-Trimethylphenoxy) propoxy]phthalic acid | 146–147 | 100 | Found; C, 63.91; H, 6.53; $C_{20}H_{22}O_6H_2O$ Requires; C, 63.82; H, 6.43% |
| 173 | 4-methyl-5-(3-phenoxypropoxy) phthalic acid | 147–148 | 100 | Found; C, 65.52; H, 5.52; $C_{18}H_{18}O_6$ Requires; C, 65.45; H, 5.49% |

EXAMPLE 166

Dimethyl 4-(3-phenoxypropoxy)phthalate

A mixture of dimethyl 4-hydroxyphthalate (2.1 g; 0.01 mole), 1-bromo-3-phenoxypropane (2.15 g; 0.01 mole) and anhydrous potassium carbonate (1.52 g; 0.015 mole) in dry butanone (30 ml) was stirred at reflux overnight and the cooled mixture filtered. Evaporation in vacuo afforded the title compound in quantitative yield. $\nu$max (film) 1730, 1605 cm$^{-1}$; $\tau$(CDCl$_3$) 7.77 (2H, quintet, J 6.5 Hz); 6.16 (3H,s); 6.11 (3H, s); 5.86 (2H, t, J 6.5 Hz); 5.78 (2H, t, J 6.7 Hz); 3.20°–2.55 (7H, m); 2.19 (1H, d, J 8.5 Hz); (Found; C, 65.98; H, 5.89; $C_{19}H_{20}O_6$ requires; C, 66.27; H, 5.85%).

Similarly were prepared the compounds of Table X.

TABLE X

| EXAMPLE | COMPOUND | b.p. °C. | YIELD % | ANALYSIS |
|---|---|---|---|---|
| 167 | Dimethyl 4-(3-phenyl-propoxy) phthalate | 186°–188° (0.3mm) | 100 | Found; C, 69.33; H, 6.04; $C_{19}H_{20}O_5$ Requires; C, 69.50; H, 6.14% |
| 168 | Dimethyl 4-[3-(2,3,5-trimethyl-phenoxy)propoxy] phthalate | 234° (0.4mm) | 90 | Found; C, 68.73; H, 7.02; $C_{22}H_{26}O_6$ Requires; C, 68.38; H, 6.78% |
| 169 | Dimethyl 4-methyl-5-(3-phenyl-propoxy)phthalate | 196° (0.2mm) m.p. (MeOH) 50° | 86 | Found; C, 67.27; H, 6.39; $C_{20}H_{22}O_6$ Requires; C, 67.02; H, 6.19% |

EXAMPLE 170

4-(3-Phenoxypropoxy)phthalic acid

A stirred mixture of dimethyl 4-(3-phenoxypropoxy) phthalate (50 g, 0.145 mole), 2.5 N sodium hydroxide (570 ml) and methanol (130 ml) was heated overnight at 80° C. The clear solution was diluted with water and acidified to give the di-acid as a white crystalline solid of m.p. 155°–159° in 90% yield. Recrystallization from water-ethanol gave material of m.p. 155°–157° (Found;

EXAMPLE 174

4-(3-Phenoxypropoxy)phthalic anhydride 4-(3-phenoxypropoxy)phthalic acid (41 g; 0.134 mole) was refluxed for 30 minutes with excess acetic anhydride and the product evaporated to dryness in vacuo. Recrystallisation of the resulting white solid from ethyl acetate afforded material of m.p. 96°–98°. (Found; C, 68.48; H, 4.75; $C_{17}H_{14}O_5$ requires; C, 68.45; H, 4.73%).

The compounds in Table XII were prepared in a similar manner.

TABLE XII

| EXAMPLE | COMPOUND | m.p. °C. | YIELD % | ANALYSIS |
|---|---|---|---|---|
| 175 | 4-(3-Phenylpropoxy) phthalic anhydride | 78–80 | 100 | Found; C, 77.98; H, 4.91; $C_{17}H_{14}O_4$ Requires; C, 72.33; H, 5.00% |
| 176 | 4-[3-(2,3,5-Trimethylphenoxy) propoxy]phthalic anhydride | 117–118 | 100 | Found; C, 70.41; H, 6.01; $C_{20}H_{20}O_5$ Requires; C, 70.58; H, 5.92% |
| 177 | 4-Methyl-5-(3-phenoxypropoxy) phthalic anhydride | 135–137 | 91 | Found; C, 69.36; H, 5.27; $C_{18}H_{16}O_5$ Requires; C, 69.22; H, 5.16% |

EXAMPLE 178

3-Nitromethylene-5 and/or 6-(3-phenoxypropoxy)phthalide

To a stirred suspension of 4-(3-phenoxypropoxy)phthalic anhydride (13.6 g; 0.0472 mole) in dry ether (1 1) at 0° was added nitromethane (6.16 g; 0.102 mole) followed by a cold ethanolic solution of sodium ethoxide (from Na [1.06 g; 0.0472 mole] and ethanol [24 ml]). The resulting pink suspension was stirred for 6 hrs at 0° and water (250 ml) added. The aqueous phase was separated, acidified and extracted with ether. Evaporation of the dried (MgSO$_4$) ethereal extract in vacuo gave a yellow oil which was refluxed for 2 hrs with excess acetic anhydride to effect dehydration of the intermediate nitroacetyl benzoic acids. Evaporation of the excess anhydride afforded an oil which was chromatographed on silica gel eluting with chloroform and the yellow fraction crystallised on trituration with ethanol. Recrystallisation from ethanol gave 2.1 g (12%) of mixed phthalides of m.p. 115°–119°.

$\nu$max (mull) 1800, 1655, 1600 cm$^{-1}$. (Found; C, 63.39; H, 4.71; N, 3.65; $C_{18}H_{15}NO_6$ requires; C, 63.34; H, 4.43; N, 4.10%).

Compounds 14 and 15 in Table XIII were similarly prepared. The increased yield of compound 16 was obtained by dropwise addition of base over 2 hrs to a mixture containing one-third of the quantity of anhydride; this being the preferred procedure

EXAMPLE 186

5-(3-Phenoxypropoxy)indan-1,3-dione

A solution of dimethyl 4-(3-phenoxypropoxy) phthalate (13.6 g, 0.0395 mole) in ethyl acetate (12 ml) was added to a 50% dispersion of sodium hydride in mineral oil (2.54 g) and the mixture heated at reflux for 4 hrs. After cooling, the mixture was triturated with 50% ethanol, ether and the yellow solid filtered off and added to a hot (70°–80° C.) 10% solution of hydrochloric acid (150 ml). After 2 mins a yellow oily solid separated which was isolated by decantation and taken up in acetone from which it crystallised on concentration to give 2.533 g (22%) of material of m.p. 91°–94° C., $\nu$max (mull) 1740, 1710, 1605 cm$^{-1}$; $\tau$(DMSO) 7.78 (2H quintet; J 6.4 Hz); 6.68 (2H, s); 5.83 (2H, t, J 6.4 Hz); 5.62 (2H, t, J 6.4 Hz); 3.21–2.44 (7H, m); 2.12 (1H, m). (Found; C, 72.97; H, 5.61; $C_{18}H_{16}O_4$ requires; C, 72.96; H, 5.44%).

TABLE XIII

| EXAMPLE | COMPOUND | m.p. °C. | YIELD % | ANALYSIS |
|---|---|---|---|---|
| 179 | 3-Nitromethylene-5 and/or 6-(3-phenylpropoxy)phthalide | 139–141 | 10 | Found; C, 66.44; H, 4.70; N, 4.24; $C_{18}H_{15}NO_5$ Requires; C, 66.46; H, 4.65; N, 4.31% |
| 180 | 3-Nitromethylene-5 and/or 6-[3-(2,3,5-trimethylphenoxy)propoxy]phthalide | 162–164 | 10 | Found; C, 65.75; H, 5.78; N, 3.42; $C_{21}H_{21}NO_6$ Requires; C, 65.79; H, 5.52; N, 3.65% |
| 181 | 5 and/or 6-methyl-3-nitromethylene-6 and/or 5-(3-phenoxypropoxy) phthalide | 152–154 | 37 | Found; C, 64.17; H, 5.01; N, 3.83; $C_{19}H_{12}NO_6$ Requires; 64.22; H, 4.82; N, 3.94% |

EXAMPLE 182

2-Nitro-5-(3-phenoxypropoxy)indan-1,3-dione

A solution of the mixed 3-nitromethylene-5 and/or 6-(3-phenoxypropoxy)phthalides (1.026 g; 0.003 mole) in ethanol free chloroform (30 ml) was treated with dry triethylamine (0.42 ml) and the red solution stirred overnight. The solvent was removed in vacuo and the product partitioned between water and ether. Evaporation of the aqueous phase gave 0.889 g of triethylamine salt of the title compound as a red oil.

$\nu$max (CHCl$_3$) 2980, 1700, 1640, 1600 cm$^{-1}$; $\tau$(CDCL$_3$), 8.72 (9H, t, J 7.2 Hz) 7.75 (2H, quintet, J 6 Hz); 6.87 (6H, quartet, J7.2 Hz); 5.86 (2H, t, J 6 Hz); 5.75 (2H, t, J 6 Hz); 3.19–2.26(8H, m); 1.92 (2H, broad exchangeable). A sample was converted to the sodium salt which had m.p. 218°–220° (dec.). (Found; C, 57.06; H, 4.30, N, 3.76; $C_{18}H_{14}NNaO_6$ H$_2$O requires; C, 56.70; H, 4.23; N, 3.67%).

By the same procedure were prepared the compounds in Table XIV.

EXAMPLE 187

2-Nitro-5-(3-phenoxypropoxy)-indan-1,3-dione

A suspension of 5-(3-phenoxypropoxy)-indan-1,3-dione (0.296 gm, 0.001 mole) was suspended in dry ether (10 ml) and cooled to 0° C. The stirred mixture was treated with fuming nitric acid (1 ml) added dropwise over 15 mins and stirred in the ice bath for 1 hr. The mixture was then stirred at r.t. for a further 1½ hrs. During this time all the solid dissolved leaving a deep yellow solution. Dilute hydrochloric acid (20 ml) was added and the ether evaporated in vacuo. A yellow gum formed which solidified on scratching to give 0.25 gm of yellow solid which had mp 77°–79° C.(d). (73%) (Found; C, 60.71; H, 4.58; N, 3.66; $C_{18}H_{15}NO_6 \cdot 0.75H_2O$ requires; C, 60.92; H, 4.69; N, 3.95%).

TABLE XIV

| EXAMPLE | COMPOUND | m.p. °C. of sodium salt | YIELD % | ANALYSIS |
|---|---|---|---|---|
| 183 | 2-Nitro-5-(3-phenylpropoxy)indan-1,3-dione | 217° (dec) | 30 | Found; C, 59.36; H, 4.41; N, 3.97; $C_{18}H_{14}NNaO_5 \cdot H_2O$ Requires; C, 59.18; H, 4.41; N, 3.83% |
| 184 | 2-Nitro-5-[3-(2,3,5-trimethyl phenoxy)propoxy]indan-1,3-dione | 263°–266° (dec) | 78 | Found; C, 61.01; H, 5.01 N, 3.46; $C_{21}H_{20}NNaO_6 0.5H_2O$ Requires; C, 60.87; H, 5.11, N, 3.38% |
| 185 | 5-Methyl-2-nitro-6-(3-phenoxypropoxy)indan-1,3-dione | indefinate | 45 | Found; C, 59.16; H, 4.91; N, 3.61; Na, 5.50; $C_{19}H_{16}NNaO_6$ 0.5H$_2$O Requires; C, 59.07; H, 4.44; N, 3.63; Na, 5.95% |

EXAMPLE 188

2-Cyano-5-(3-phenoxypropoxy)indan-1,3-dione

A mixture of dimethyl 4-(3-phenoxypropoxy)phthalate (6.5 g; 0.019 mole), acetonitrile (10 ml) and sodium hydride (0.69 g of 100%) was stirred at 100° for 6 hours and dry ether added to the cooled yellow product. The solid which separated was filtered off, dissolved in water and the solution strongly acidified with concentrated hydrochloric acid. Filtration of the precipitated solid gave the title compound which recrystallised from ethanol dilute hydrochloric acid with mp 148°–150° (dec) and in 86% yield. (Found; C, 69.00; H, 4.90; N, 4.41; $C_{19}H_{15}NO_4 \cdot 0.5H_2O$ requires; C, 69.08; H, 4.88; N, 4.24%).

The compounds in Table XV were prepared in the same way.

TABLE XV

| Example | Compound | m.p. °C. | Yield % | Analysis |
|---|---|---|---|---|
| 189 | 2-Cyano-5-(2-phenylethoxy)indan-1,3-dione | 168°(dec) | 26 | Found; C, 72.08; H, 4.61; N, 4.97; $C_{18}H_{13}NO_3 \cdot 0.5H_2O$ required; C, 71.99; H, 4.70; N, 4.67% |
| 190 | 2-Cyano-5-[3-(2,3,5-trimethylphenoxy)propoxy]indan-1,3-dione | 191°–195° (dec) | 69 | Found; C, 72.87; H, 5.80; N, 4.22 $C_{22}H_{21}NO_4$ requies; C, 72.71; H, 5.82; N, 3.86% |
| 191 | 2-Cyano-5-methyl-6-(3-phenoxypropoxy)indan-1,3-dione | 140°–143° (dec) | 12 | Found; C, 71.58; H, 5.19; N, 3.93; $C_{20}H_{17}NO_4$ requires; C, 71.63; H, 5.11; N, 4.18% |

EXAMPLE 192

Methyl 2-hydroxy-4-(3-phenoxypropoxy) benzoate

Methyl 2,4-dihydroxybenzoate (33.6 g; 0.2 mole) and anhydrous sodium carbonate (34.8 g; 0.3 mole) in dry butanone (300 ml) were stirred at reflux during the addition of 1-bromo-3-phenoxypropane (43.0 g; 0.2 mole) in butanone (50 ml) and the mixture stirred at reflux for 24 hours. The mixture was cooled and filtered and the filtrate evaporated to a white solid. Recrystallisation from ethanol gave 38.7 g (64%) of material of mp 90°–92°, $\nu$max (mull) 1660, 1615, 1598, 1580 cm$^{-1}$. (Found; C, 67.69; H, 6.22; $C_{17}H_{18}O_5$ requires; C, 67.54; H, 6.00%).

Using this procedure the compounds of Table XVI were prepared.

TABLE XVI

| Example | Compound | m.p. °C. | Yield % | Analysis |
|---|---|---|---|---|
| 193 | Methyl 4-[3-(4-fluorophenoxy)propoxy]2-hydroxy-3-methylbenzoate | 92–94 | 45 | Found; C, 64.65; H, 6.04; $C_{18}H_{19}FO_5$ requires; C, 64.66; H, 5.73% |
| 194 | Methyl 2-hydroxy-4-[3-(2,3,5-trimethylphenoxy)propoxy]benzoate | 97–98 | 47 | Found; C, 69.56; H, 7.34; $C_{20}H_{24}O_5$ requires; C, 69.75; H, 7.02% |
| 195 | Methyl 2-hydroxy-4-(3-phenylpropoxy)benzoate | 60–62 | 45 | Found; C, 71.31; H, 6.34; $C_{12}H_{18}O_4$ requires; C, 71.16; H, 6.45% |

EXAMPLE 196

2-Hydroxy-4-(3-phenoxypropoxy)benzoic acid

A mixture of methyl 2-hydroxy-4-(3-phenoxypropoxy) benzoate (18.55 g), methanol (40 ml) and 10% aqueous sodium hydroxide (100 ml) was stirred at 60° until a clear solution was obtained, then cooled and acidified. The precipitated solid was collected and recrystallised from cyclohexane-ethanol to give 15.09 g (85%) of acid of mp 161°. (Found; C, 66.46; H, 5.71; $C_{16}H_{16}O_5$ requires; C, 66.65; H, 5.59%).

Similarly were prepared the compounds of Table XVII.

TABLE XVII

| Example | Compound | m.p. °C. | Yield % | Analysis |
|---|---|---|---|---|
| 197 | 4-[3-(4-Fluorophenoxy)propoxy]2-hydroxy-3-methylbenzoic acid | 160–161 | 97 | Found; C, 63.20; H, 5.21; $C_{17}H_{17}FO_5 \cdot 0.25H_2O$ requires; C, 62.86; H, 5.43%. |
| 198 | 2-Hydroxy-4-[3-(2,3,5-trimethylphenoxy)propoxy]benzoic acid | 181–183 | 48 | Found; C, 68.05; H, 6.85; $C_{19}H_{22}O_5 \cdot 0.25H_2O$ requires; C, 68.14; H, 6.77%. |
| 199 | 2-Hydroxy-4-(3-phenylpropoxy)benzoic acid | 159–162 | 98 | Found; C, 70.85; H, 6.04; requires; C, 70.57; H, 5.92%. |

EXAMPLE 200

2-Acetoxy-4-(3-phenoxypropoxy) benzoic acid

A solution of 2-hydroxy-4-(3-phenoxypropoxy) benzoic acid (13.07 g) in a 1:1 mixture of acetic acid: acetic anhydride (80 ml) was refluxed for 1.5 hours. The cooled mixture was poured into water and the precipitated product filtered off and recrystallised from ethanol to give 14.22 g (95%) of acetate of mp 130°–132°. (Found; C, 65.31; H, 5.79; $C_{18}H_{18}O_6$ requires; C, 65.45; H, 5.49%).

By this procedure those compounds in Table XVII were synthesised.

TABLE XVIII

| Example | Compound | m.p. °C. | Yield % | Analysis |
|---|---|---|---|---|
| 201 | 2-Acetoxy-4-[3-(4- | 127–129 | 93 | Found; C, 63.21; H, 5.52; $C_{19}H_{19}FO_6$ |

TABLE XVIII-continued

| Example | Compound | m.p. °C. | Yield % | Analysis |
|---|---|---|---|---|
| | fluorophenoxy)-propoxy]-3-methyl-benzoic acid | | | requires; C, 62.98; H, 5.28% |
| 202 | 2-Acetoxy-4-[3-(2,3,5-trimethylphenoxy)propoxy]benzoic acid | 140–143 | 93 | Found; C, 68.22; H, 6.66; $C_{21}H_{24}O_6$ requires; C, 67.73; H, 6.50% |
| 203 | 2-Acetoxy-4-(3-phenylpropoxy)benzoic acid | 119–122 | 87 | Found; C, 68.69; H, 5.91; $C_{18}H_{18}O_5$ requires; C, 68.78; H, 5.77% |

EXAMPLE 204

3-Cyano-4-hydroxy-7-(3-phenoxypropoxy) coumarin

2-Acetoxy-4-(3-phenoxypropoxy) benzoic acid (13.80 g) was treated with thionyl chloride (20 ml) in dry benzene (100 ml).

The mixture was refluxed for 5 hours and the solvent and excess thionyl chloride removed under reduced pressure. The residue, a pale yellow oil, weighed 14.50 g (100%).

This acid chloride, dissolved in dry ether (75 ml) was added dropwise with stirring, to a refluxing mixture of ethyl cyanoacetate (14.92 g) in dry ether (275 ml), and sodium hydride (50%, 6.00 g). The reaction was stirred and refluxed for a further 18 hours. After cooling, the reaction mixture was poured into water (500 ml) containing sodium hydroxide (2.5 g) and stirred vigorously for ½ hour. The aqueous layer was separated and washed with ether three times. Acidification of the aqueous solution with dilute hydrochloric acid gave a cream colored precipitate, which was collected by filtration, washed with water and dried. Yield 12.03 mp 160°–70°. Two crystallizations from ethanol yielded the analytically pure hemiethanolate 4.88 g (36%) mp 178° (Found; C, 66.44; H, 5.31; N, 3.62 $C_{19}H_{15}NO_5$, $0.5C_2H_5OH$ requires; C, 66.65; H, 5.03; N, 3.88).

The compounds of Table XIX were similarly prepared.

mg/ml ovalbumin (Sigma Grade III) and 50 µg/ml heparin was injected by the same route. Five minutes after challenge the rats were stunned and bled and the peritoneal fluids collected into polycarbonate tubes in ice. After centrifugation at 150 g for 5 minutes the supernatants were combined, heated in a boiling water bath for 5 minutes, cooled and stored at $-20°$ C. The combined peritoneal fluids contained SRS-A and were used in the antagonism studies.

The SRS-A assays were carried out on isolated strips of guinea pig ileum in tyrode solution containing atropine $5 \times 10^{-7}$ M and mepyramine $10^{-6}$ M as described by W. E. Brocklehurst, J. Physiology, 151, 416 (1960).

The activity of the antagonists was determined by their ability to reduce submaximal responses induced by SRS-A. The antagonists were added to 4 ml bath in 0.1 ml volumes in aqueous solution half a minute before the addition of SRS-A and were present during induced contraction. Two or three concentrations of antagonists were used and the percentage inhibition of the SRS-A response plotted against the bath concentration of antagonist. The line of best fit was drawn and the concentration to cause 50% inhibition $IC_{50}$ read graphically.

Passive Cutaneous Anaphylaxis

Serum containing heat labile homocytotropic antibody was raised in rats to crystallized ovalbumin XOA by the method of Mota (I. Mota, Immunology, 7,681

TABLE XIX

| Example | Compound | m.p. °C. | Yield % | Analysis |
|---|---|---|---|---|
| 205 | 3-Cyano-7-[3-(4-fluorophenoxy)propoxy]-4-hydroxycoumarin | 212–215 | 39 | |
| 206 | 3-Cyano-4-hydroxy-7-[3-(2,3,5-Trimethylphenoxy)-propoxy]coumarin | 157–158 | 10 | Found; C, 63.86; H, 5.74; N, 3.53; $C_{22}H_{21}NO_5 \cdot 2H_2O$ requires; C, 63.61; H, 6.07; N, 3.37% |
| 207 | 3-Cyano-4-hydroxy-7-[3-phenoxypropoxy) coumarin | 214 | 25 | Found; C, 70.76; H, 4.80; N, 4.06; $C_{19}H_{15}NO_4$ requires; C, 71.02; H, 4.70; N, 4.36% |

BIOLOGICAL DATA

SRS-A Antogonist Activity

The compounds have been evaluated as direct antagonists of slow reacting substance of anaphylaxis (SRS-A) by assay using the isolated guinea pig ileum.

SRS-A rat was obtained from the peritoneal cavity of the rat after passive peritoneal anaphylaxis by a method based on that of R. P. Orange, D. J. Stechschulte and K. F. Austen, J. Immunology, 105 1087 (1970) as described by B. A. Spicer, J. W. Ross and H. Smith, Clin. exp. Immunol. 1975, 21, 419. The sensitizing serum containing reaginic antibody was produced in rats as described by B. A. Spicer, et. al. ibid.

2 ml of a 1 in 5 dilution of the sensitizing serum was injected by the peritoneal route into recipient rats and after 2 hours, 5 ml of tyrode solution containing 0.4

(1964)) using Bordettela pertussis vaccine as adjuvant.

Passive cutaneous anaphylaxis (PCA) was carried out by a method based on that of Ovary and Bier (A. Ovary and O. G. Bier, Proc. Soc. Exp. Biol. Med 81, 584, (1952)) as modified by Goose and Blair.

Male Wistar rats of 250–300 g were given 0.1 ml of each of six twofold serial dilutions of pooled antiserum in 0.9% saline injected intradermally into separate sites on their shaved backs. Later (72 hr) the animals were challenged by intravenous injection of 0.3 ml of a 1% solution of ovalbumin in an isotonic solution of saline buffered with 0.5 M, pH 7.2, Sorenson Buffer (PBS), mixed with 0.2 ml of a 5% solution of Pontamine Sky Blue (6BX C.I. 24410, Raymond A. Lamb,London) in isotonic saline. The rats were killed after 20 min and the diameter of the blue wheals at the antibody injection sites was measured on the outer surface of the skin. The starting dilution of the serum was adjusted so that there was no response, after challenge, at the injection site of the highest dilution and a maximum response at the lowest dilutions. Typically six twofold serial dilutions of the serum from ¼ to 1/128 were used.

Compounds were tested for their ability to reduce the diameter of the wheals at those intradermal sites which in control animals gave less than maximum response. Each dose of the compound was administered intravenously to six rats in isotonic saline, adjusted to pH7 with sodium bicarbonate if necessary (2 ml/kg body weight) just before intravenous challenge with ovalbumin. Control groups of six animals were given the same volume of carrier fluid at the same time.

The results were calculated as follows. % inhibition of PCA = 100 (1−a/b) where a = the sum of the diameters of the wheals produced in the test animal at the sites of antibody dilutions as used in control groups and b = the mean sum of the diameters of the wheals produced in the control group of animals at those antibody sites where at least five out of six of the animals gave less than maximum response. A typical variation in the control group of animals was SEN±6%.

The dose of the compound required to inhibit the PCA response by 50% was obtained from the log dose-response curve.

BIOLOGICAL RESULTS

| Example | Formula | SRS-A antagonism on Guinea Pig Ileum Approximate concentration to give 50% inhibition of a less than maximal response to SRS-A | Rat PCA Dose given i.v. to effect a 50% inhibition of the PCA response |
|---|---|---|---|
| 114 | (structure) | $10^{-8}$M | <1mg/Kg |
| 115 | (structure) | $10^{-5}$M | >2mg/Kg |
| 116 | (structure) | $10^{-6}$M | <1mg/Kg |
| 117 | (structure) | $10^{-5}\text{--}10^{-6}$M | 1 mg/kg |
| 118 | (structure) | $10^{-6}$M | >2mg/Kg |
| 119 | (structure) | $10^{-6}$M | ca 2mg/Kg |

-continued

BIOLOGICAL RESULTS

| Example | Formula | SRS-A antagonism on Guinea Pig Ileum Approximate concentration to give 50% inhibition of a less than maximal response to SRS-A | Rat PCA Dose given i.v. to effect a 50% inhibition of the PCA response |
|---|---|---|---|
| 120 | Ac—⟨phenyl⟩—(CH₂)₃—O—⟨chromone with OH, NO₂⟩ | $10^{-6}$ M | ca 2mg/Kg |
| 121 | ⟨phenyl⟩—(CH₂)₄—O—⟨chromone with OH, NO₂⟩ | $10^{-6}$ M | >2mg/Kg |
| 122 | Cl—⟨phenyl⟩—(CH₂)₄O—⟨chromone with OH, NO₂⟩ | $10^{-6}$ M | >2mg/Kg |
| 123 | Me—⟨phenyl⟩—(CH₂)₄—O—⟨chromone with OH, NO₂₂⟩ | $10^{-6}$ M | >2mg/Kg |
| 124 | Cl—⟨phenyl⟩—O—CH₂—O—⟨chromone with OH, NO₂⟩ | | >2mg/Kg |
| 125 | ⟨phenyl⟩—O(CH₂)₂O—⟨chromone with OH, NO₂⟩ | $10^{-5}$ M | >2mg/Kg |
| 126 | ⟨phenyl⟩—O(CH₂)₂O—⟨chromone with OH, NO₂⟩ | $10^{-5}$ M | <1mg/Kg |
| 127 | Ac—⟨phenyl with HO, Prⁿ⟩—O(CH₂)₂O—⟨chromone with OH, NO₂⟩ | | ca 2mg/kg |
| 128 | ⟨phenyl⟩—O(CH₂)₃O—⟨chromone with OH, NO₂⟩ | $10^{-6}$ M | >2mg/Kg |

-continued

BIOLOGICAL RESULTS

| Example | Formula | SRS-A antagonism on Guinea Pig Ileum Approximate concentration to give 50% inhibition of a less than maximal response to SRS-A | Rat PCA Dose given i.v. to effect a 50% inhibition of the PCA response |
|---|---|---|---|
| 129 | Ph-O(CH$_2$)$_3$-O-[benzene ring with OH, NO$_2$ substituents and fused pyranone] | $10^{-6}$M | <1 mg/Kg |
| 130 | Ph-O(CH$_2$)$_3$-O-[benzene ring with Me, OH, NO$_2$ substituents and fused pyranone] | $10^{-6}$M | >2 mg/Kg |
| 131 | Ph-O(CH$_2$)$_3$-O-[benzene ring with Pr$^n$, OH, NO$_2$ substituents and fused pyranone] | $10^{-6}$M | <1 mg/Kg |
| 132 | Ph-O(CH$_2$)$_3$-O-[benzene ring with Et, OH, NO$_2$ substituents and fused pyranone] | $10^{-5}$M | <1 mg/Kg |
| 133 | Cl-C$_6$H$_4$-O(CH$_2$)$_3$-O-[benzene ring with OH, NO$_2$ substituents and fused pyranone] | $10^{-6}$M | <1 mg/Kg |
| 134 | HO$_2$C-C$_6$H$_4$-O(CH$_2$)$_3$-O-[benzene ring with OH, NO$_2$ substituents and fused pyranone] | $10^{-5}$M | <1 mg/Kg |
| 135 | MeO$_2$C-C$_6$H$_4$-O(CH$_2$)$_3$-O-[benzene ring with OH, NO$_2$ substituents and fused pyranone] | $10^{-5}$M | <1 mg/Kg |
| 136 | Ac-C$_6$H$_4$-O(CH$_2$)$_3$-O-[benzene ring with OH, NO$_2$ substituents and fused pyranone] | $10^{-6}$M | <1 mg/Kg |

-continued
BIOLOGICAL RESULTS

| Example | Formula | SRS-A antagonism on Guinea Pig Ileum Approximate concentration to give 50% inhibition of a less than maximal response to SRS-A | Rat PCA Dose given i.v. to effect a 50% inhibition of the PCA response |
|---|---|---|---|
| 137 | | $10^{-5}$M | <1mg/Kg |
| 138 | | $10^{-6}$M | ca 2mg/Kg |
| 139 | | $10^{-7}$M | |
| 140 | | $10^{-5}$M | <1mg/Kg |
| 141 | | $10^{-5}$M | <1mg/Kg |
| 142 | | $10^{-6}$–$10^{-7}$M | <1mg/kg |
| 143 | | $10^{-5}$M | <2mg/Kg |
| 144 | | $10^{-7}$M | 2mg/Kg |

-continued

BIOLOGICAL RESULTS

| Example | Formula | SRS-A antagonism on Guinea Pig Ileum Approximate concentration to give 50% inhibition of a less than maximal response to SRS-A | Rat PCA Dose given i.v. to effect a 50% inhibition of the PCA response |
|---|---|---|---|
| 145 | [structure: Ac, Et, HO, OH, O—CH₂—CH(OH)—CH₂—O—chromone with NO₂] | $10^{-6}$M | 2 mg/kg |
| 146 | [structure: Ac, HO, Pr$^n$, O—CH₂—CH(OH)—CH₂—O—chromone with NO₂] | | |
| 147 | [structure: Ac, HO, Pr$^n$, O—CH₂—CH(OH)—CH₂—O—chromone with NO₂, Me] | $10^{-8}$ | <2 mg/kg |
| 148 | [structure: Ac, HO, Pr$^n$, O—CH₂—CH(OH)—CH₂—O—chromone with NO₂, Pr$^n$] | $10^{-7}$M | <1 mg/Kg |
| 149 | [structure: EtCO, HO, Pr$^n$, OCH₂CH(OH)CH₂O—chromone with NO₂] | | 2 mg/kg |
| 150 | [structure: Ph—O(CH₂)₄O—chromone with NO₂] | $10^{-6}$M | ca 1 mg/Kg |
| 151 | [structure: Ph—O(CH₂)₅O—chromone with NO₂] | $10^{-6}$M | >2 mg/Kg |
| 152 | [structure: Ph—O(CH₂)₅O—chromone with NO₂] | $10^{-6}$M | 2 mg/Kg |
| 153 | [structure: Ph—O—(CH₂)₆—O—chromone with NO₂] | $10^{-7}$M | >2 mg/Kg |

-continued
BIOLOGICAL RESULTS

| Example | Formula | SRS-A antagonism on Guinea Pig Ileum Approximate concentration to give 50% inhibition of a less than maximal response to SRS-A | Rat PCA Dose given i.v. to effect a 50% inhibition of the PCA response |
| --- | --- | --- | --- |
| 154 | Ph—O(CH$_2$)$_6$O-[chromone-OH-NO$_2$] | $10^{-5}$M | 1–2 mg/Kg |
| 155 | (2-Me-C$_6$H$_4$)—O(CH$_2$)$_3$O-[chromone-OH-NO$_2$] | $10^{-7}$M | 1–2 mg/Kg |
| 156 | (3-Me-C$_6$H$_4$)—O(CH$_2$)$_3$O-[chromone-OH-NO$_2$] | $10^{-6}$M | <2 mg/Kg |
| 157 | (4-Me-C$_6$H$_4$)—O(CH$_2$)$_3$O-[chromone-OH-NO$_2$] | $10^{-6}$M | <2 mg/Kg |
| 158 | (4-MeO-C$_6$H$_4$)—O(CH$_2$)$_3$O-[chromone-OH-NO$_2$] | $10^{-6}$M | <2 mg/Kg |
| 159 | (4-F-C$_6$H$_4$)—O(CH$_2$)$_3$O-[chromone-OH-NO$_2$] | $10^{-7}$M | <1 mg/Kg |
| 160 | (4-NC-C$_6$H$_4$)—O(CH$_2$)$_3$O-[chromone-OH-NO$_2$] | $10^{-5}$M | <1 mg/Kg |
| 161 | (4-Ph-C$_6$H$_4$)—O(CH$_2$)$_3$O-[chromone-OH-NO$_2$] | $10^{-5}$M | |

-continued
BIOLOGICAL RESULTS

| Example | Formula | SRS-A antagonism on Guinea Pig Ileum Approximate concentration to give 50% inhibition of a less than maximal response to SRS-A | Rat PCA Dose given i.v. to effect a 50% inhibition of the PCA response |
|---|---|---|---|
| 162 | (structure) | $10^{-5}$ M | >2 mg/Kg |
| 163 | (structure) | $10^{-7}$ M | <1 mg/Kg |
| 164 | (structure) | $10^{-7}$ | 1 mg/kg |
| 165 |  |  | 1 mg/kg |
| 166 |  | $10^{-7}$ | <1 mg/kg |

| Example No. | Biological Results SRS-A antagonism on Guinea Pig ileum Approximate concentration to give 50% inhibition of a less than maximal response to SRS-A | Rat PCA Dose given i.v. to effect a 50% inhibition of PCA response |
|---|---|---|
| 182 sodium salt | $10^{-7}$ | <1 mg/kg |
| 183 | $10^{-5} – 10^{-6}$ | <1 mg/kg |
| 184 | $10^{-6}$ | 1 mg/kg |
| 185 | $10^{-6}$ |  |
| 188 | $10^{-6}$ | >2 mg/kg |
| 189 | $10^{-6}$ |  |
| 204 | $10^{-6}$ | 2 mg/kg |

What we claim is:

1. A compound of the formula (I):

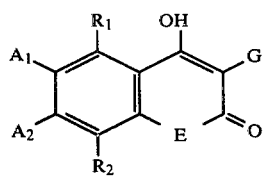

or a pharmaceutically acceptable salt thereof wherein one of $A_1$ or $A_2$ is a group of the formula (II)

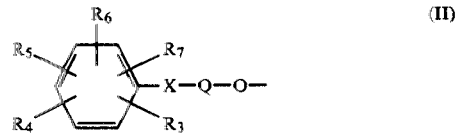

and $R_1$, $R_2$ and the one of $A_1$, or $A_2$ which is not a group of the formula (II) are the same or different and each is hydrogen, lower alkyl, lower alkoxy, lower alkenyl, or lower alkynyl; provided that at least one of $R_1$, $R_2$, $A_1$ and $A_2$ is hydrogen, E is covalent bond; G is nitro or cyano; X is methylene; and Q is alkylene of 1 to 8 carbon atoms, 1 methylene group within the group Q, other than a methylene covalently bound to an ether oxygen, being unsubstituted or substituted by hydroxyl, and $R_3$, $R_4$, $R_5$, $R_6$ and $R_7$ are each hydrogen, halogen, nitro, hydroxy, cyano, carboxyl, amino, lower alkyl, lower alkenyl, lower alkynyl, lower alkoxy, lower alkoxy carbonyl, lower alkanoyl, lower alkanoyloxy, mono- or di-lower alkyl amino, mono- or di-lower alkanoyl amino, phenyl, lower alkylphenyl, phenoxycarbonyl, or benzyloxycarbonyl.

2. A compound according to claim 1 wherein $R_1$, $R_2$ and $A_1$ are the same or different and each is hydrogen or lower alkyl, and $A_2$ is a substituent of the formula (II).

3. A compound according to claim 2 wherein one of $R_3$ to $R_7$ is hydrogen.

4. A compound according to claim 2 wherein two of $R_3$ to $R_7$ are hydrogen.

5. A compound according to claim 4 wherein $R_3$ is hydrogen, lower alkyl, lower alkoxy, lower alkanoyl, lower alkanoyloxy, lower alkoxycarbonyl, phenyl, cyano, carboxyl, halogen, nitro, amino, mono- or di-lower alkylamino, or mono- or di-lower alkanoyl amino, $R_4$ is hydrogen, lower alkyl, lower alkoxy, lower alkanoyl, lower alkanoyloxy or lower alkoxy carbonyl, and $R_5$ is hydrogen or lower alkyl; and $R_6$ and $R_7$ are both hydrogen.

6. A compound according to claim 1 wherein $R_3$ is lower alkyl and $R_4$ to $R_7$ are all hydrogen.

7. A compound according to claim 6 wherein $R_3$ is methyl, ethyl or n-propyl.

8. A compound according to claim 7 wherein $R_3$ is n-propyl at position 2' of the phenyl ring of substituent (II).

9. A compound according to claim 1 wherein $R_3$ is fluorine and $R_4$ to $R_7$ are all hydrogen.

10. A compound according to claim 9 wherein $R_3$ is fluorine at 4' at the phenyl ring of substituent (II).

11. A compound according to claim 1 wherein $R_3$ is fluorine, $R_4$ is lower alkyl, and $R_5$ to $R_7$ are all hydrogen.

12. A compound according to claim 11 wherein $R_4$ is n-propyl.

13. A compound according to claim 12 wherein $R_3$ is at position 4' and $R_4$ is at position 2' of the phenyl ring of substituent (II).

14. A compound according to claim 5 wherein $R_3$ is lower alkanoyl, $R_4$ is hydroxy, $R_5$ is lower alkyl, $R_6$ and $R_7$ are hydrogen.

15. A compound according to claim 14 wherein $R_3$ is at position 3', $R_4$ is at position 4' and $R_5$ is at position 2' of the phenyl ring of substituent (II).

16. A compound according to claim 15 wherein $R_3$ is acetyl and $R_5$ is n-propyl.

17. A compound according to claim 1 wherein $R_1$ and $R_2$ and the one of $A_1$ and $A_2$ which is not a substituent of formula (II) all represent hydrogen.

18. A compound according to claim 17 wherein $R_3$ to $R_7$ are all hydrogen.

19. A compound according to claim 1 wherein Q represents ethylene.

20. A compound according to claim 1 wherein Q represents ethylene, propylene, butylene or pentylene.

21. A compound according to claim 20 wherein one methylene group other than a methylene bound to an ether oxygen is substituted with hydroxyl.

22. A compound according to claim 1 wherein Q is methylene or ethylene.

23. A compound according to claim 1 wherein Q is propylene, butylene, pentylene or hexylene.

24. A compound according to claim 1 wherein Q is propylene substituted by hydroxyl, butylene substituted by hydroxyl, pentylene substituted by hydroxyl or hexylene substituted by hydroxyl.

25. A compound according to claim 1 wherein Q is 2-hydroxypropylene.

26. A compound according to claim 1 wherein G is nitro.

27. A compound according to claim 26 selected from the group consisting of:
5-(2-[4-fluorophenyl]ethoxy)-2-nitroindan-1,3-dione
5-(3-[4-acetylphenyl]-propoxy)-2-nitroindan-1,3-dione
2-nitro-5-(3-[2-n-propylphenyl]-butoxy)indan-1,3-dione,
and the pharmaceutically acceptable salts thereof.

28. A compound according to claim 1 wherein G is cyano.

29. A compound according to claim 28 selected from the group consisting of:
2-cyano-5-(2-phenylethoxy)indan-1,3-dione.
2-cyano-5-(2-phenylpropoxy)indan-1,3-dione.
2-cyano-5-(4-[4-acetyl-3-hydroxy-2-n-propylphenyl]-butoxy)indan-1,3-dione.
and the pharmaceutically acceptable salts thereof.

30. A compound according to claim 29 selected from the group consisting of:
2-cyano-5-(2-phenylethoxy)indan-1,3-dione,
2-cyano-5-(3-phenylpropoxy)indan-1,3-dione,
2-cyano-5-(4-[4-acetyl-3-hydroxy-2-n-propylphenyl]-butoxy)indan-1,3-dione,
and the pharmaceutically acceptable salts thereof.

31. A pharmaceutical composition useful for the inhibition in humans of the release of mediators of allergic response and for the inhibition in humans of the action of said mediators which comprises an effective amount of a compound of the formula (I):

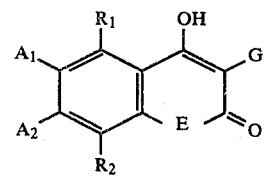

or a pharmaceutically acceptable salt thereof wherein one of $A_1$ or $A_2$ is a group of the formula (II):

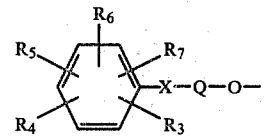

and $R_1$, $R_2$ and the one of $A_1$ or $A_2$ which is not a group of the formula (II) are the same or different and each is hydrogen, lower alkyl, lower alkoxy, lower alkenyl or lower alkynyl; provided that at least one of $R_1$, $R_2$, $A_1$ and $A_2$ is hydrogen, E is a covalent bond; G is nitro or cyano; X is methylene;

and Q is alkylene of 1 to 8 carbon atoms, 1 methylene group within the group Q, other than a methylene covalently bound to an ether oxygen, being unsubstituted or substituted by hydroxyl, and $R_3$, $R_4$, $R_5$, $R_6$ and $R_7$ are each hydrogen, halogen, nitro, hydroxy, cyano, carboxyl, amino, lower alkyl, lower alkenyl, lower alkynyl, lower alkoxy, lower alkoxy carbonyl, lower alkanoyl, lower alkanoyloxy, mono- or di-lower alkyl amino, mono- or di-lower alkanoyl amino, phenyl, lower alkylphenyl, phenoxycarbonyl, or benzyloxycarbonyl, in combination with a pharmaceutically acceptable carrier.

32. A composition according to claim 33 wherein $R_1$, $R_2$ and $A_1$ are the same or different and each is hydrogen or lower alkyl, and $A_2$ is a substituent of the formula (II).

33. A composition according to claim 32 wherein one of $R_3$ to $R_7$ is hydrogen.

34. A composition according to claim 32 wherein two of $R_3$ and $R_7$ are hydrogen.

35. A composition according to claim 34 wherein $R_3$ is hydrogen, lower alkyl, lower alkoxy, lower alkanoyl, lower alkanoyloxy, lower alkoxycarbonyl, phenyl, cyano, carboxyl, halogen, nitro, amino, mono- or, di-lower alkyl amino, or mono- or di-lower alkanoyl amino, $R_4$ is hydrogen, loweralkyl, lower alkoxy, lower alkanoyl, lower alkanoyloxy or lower alkoxy carbonyl, and $R_5$ is hydrogen or lower alkyl; and $R_6$ and $R_7$ are both hydrogen.

36. A composition according to claim 31 wherein $R_3$ is lower alkyl and $R_4$ to $R_7$ are all hydrogen.

37. A composition according to claim 36 wherein $R_3$ is methyl, ethyl or n-propyl.

38. A composition according to claim 37 wherein $R_3$ is n-propyl at position 2' of the phenyl ring of substituent (II).

39. A composition according to claim 31 wherein $R_3$ is fluorine and $R_4$ to $R_7$ are all hydrogen.

40. A composition according to claim 39 wherein $R_3$ is fluorine at 4' at the phenyl ring of substituent (II).

41. A composition according to claim 31 wherein $R_3$ is fluorine₂ $R_4$ is lower alkyl, and $R_5$ to $R_7$ are all hydrogen.

42. A composition according to claim 41 wherein $R_4$ is n-propyl.

43. A composition according to claim 42 wherein $R_3$ is at position 4' and $R_4$ is at position 2' of the phenyl ring of substituent (II).

44. A composition according to claim 34 wherein $R_3$ is lower alkanoyl, $R_4$ is hydroxy, $R_5$ is lower alkyl, $R_6$ and $R_7$ are hydrogen.

45. A composition according to claim 44 wherein $R_3$ is at position 3', $R_4$ is at position 4' and $R_5$ is at position 2' of the phenyl ring of substituent (II).

46. A composition according to claim 45 wherein $R_3$ is acetyl and $R_5$ is n-propyl.

47. A composition according to claim 31 wherein $R_1$ and $R_2$ and the one of $A_1$ and $A_2$ which is not a substituent of formula (II) are each hydrogen.

48. A composition according to claim 47 wherein $R_3$ to $R_7$ are all hydrogen.

49. A composition according to claim 31 wherein Q represents ethylene.

50. A composition according to claim 31 wherein Q represents ethylene, propylene, butylene or pentylene.

51. A composition according to claim 50 where one methylene group other than a methylene bound to an ether oxygen is substituted with hydroxyl.

52. A composition according to claim 31 wherein Q is methylene or ethylene.

53. A composition according to claim 31 wherein Q is propylene, butylene, pentylene or hexylene.

54. A composition according to claim 53 wherein Q is propylene substituted by hydroxyl, butylene substituted by hydroxyl, pentylene substituted by hydroxyl or hexylene substituted by hydroxyl.

55. A composition according to claim 54 wherein Q is 2-hydroxypropylene.

56. A composition according to claim 31 wherein G is nitro.

57. A composition according to claim 56 selected from the group consisting of:
5-(2-[4-fluorophenyl]ethoxy)-2-nitroindan-1,3-dione
5-(3-[4-acetylphenyl]-propoxy)-2-nitroindan-1,3-dione.
2-nitro-5-(3-[2-n-propylphenylphenyl]-butoxy)indan-1,3-dione,
and the pharmaceutically acceptable salts thereof.

58. A composition according to claim 31 wherein G is cyano.

59. A composition according to claim 58 selected from the group consisting of:

2-cyano-5-(2-phenylethoxy)indan-1,3-dione.
2-cyano-5-(2-phenylpropoxy)indan-1,3-dione.
2-cyano-5-(4-[4-acetyl-3-hydroxy-2-n-propylphenyl]-butoxy)indan-1,3-dione.
and the pharmaceutically acceptable salts thereof.

60. A composition according to claim 58 selected from the group consisting of:
2-cyano-5-(2-phenylethoxy)indan-1,3-dione,
2-cyano-5-(3-phenylpropoxy)indan-1,3-dione,
2-cyano-5-(4-acetyl-3-hydroxy-2-n-propylphenyl]-butoxy)indan-1,3-dione,
and the pharmaceutically acceptable salts thereof.

61. A composition according to claim 31 in the form of a microfine powder suitable for administration by insufflation.

62. A composition according to claim 31 in a form suitable for administration by injection.

63. A composition according to claim 31 in the form of an ointment cream or lotion for topical application.

64. A composition according to claim 31 in a form suitable for oral administration.

65. A method of inhibiting mediators of allergic response in humans and for inhibiting in humans the action of said mediators which comprises administering to a human in need thereof an effective amount of a compound of the formula (I):

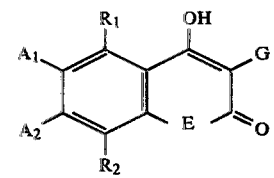

or a pharmaceutically acceptable salt thereof wherein one of $A_1$ $A_2$ is a group of the formula (II):

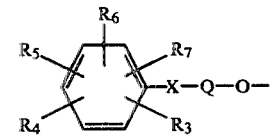

and $R_1$, $R_2$ and the one of $A_1$ or $A_2$ which is not a group of the formula (II) are the same or different and each is hydrogen, lower alkyl, lower alkoxy, lower alkenyl or lower alkynyl; provided that at least one of $R_1$, $R_2$, $A_1$ and $A_2$ is hydrogen, E is a covalent bond; G is nitro or cyano; X is methylene; and Q is alkylene of 1 to 8 carbon atoms, 1 methylene group within the group Q, other than a methylene covalently bound to an ether oxygen, being unsubstituted or substituted by hydroxyl, and $R_3$, $R_4$, $R_5$, $R_6$ and $R_7$ are each hydrogen, halogen, nitro, hydroxy, cyano, carboxyl, amino, lower alkyl, lower alkenyl, lower alkynyl, lower alkoxy, lower alkoxy carbonyl, lower alkanoyl, lower alkanoyloxy, mono- or di-lower alkyl amino, mono- or di-lower alkanoyl amino, phenyl, lower alkylphenyl, phenoxycarbonyl, or benzyloxycarbonyl, in combination with a pharmaceutically acceptable carrier.

66. A method according to claim 44 wherein $R_1$, $R_2$ and $A_1$ are the same or different and each is hydrogen or lower alkyl, and $A_2$ is a substituent of the formula (II).

67. A method according to claim 66 wherein one of $R_3$ to $R_7$ is hydrogen.

68. A method according to claim 66 wherein two of $R_3$ to $R_7$ are hydrogen.

69. A method according to claim 47 wherein $R_3$ is hydrogen, lower alkyl, lower alkoxy, lower alkanoyl, lower alkanoyloxy, lower alkoxycarbonyl, phenyl, cyano, carboxyl, halogen, nitro amino, mono- or di-lower alkyl amino, or mono- or di-lower alkanoyl amino, $R_4$ is hydrogen, lower alkyl, lower alkoxy, lower alkanoyl, lower alkanoyloxy or lower alkoxy carbonyl, and $R_5$ is hydrogen or lower alkyl; and $R_6$ and $R_7$ are both hydrogen.

70. A method according to claim 65 wherein $R_3$ is lower alkyl and $R_4$ to $R_7$ are all hydrogen.

71. A method according to claim 70 wherein $R_3$ is methyl, ethyl or n-propyl.

72. A method according to claim 71 wherein $R_3$ is n-propyl at position 2′ of the phenyl ring of substituent (II).

73. A method according to claim 65 wherein $R_3$ is fluorine and $R_4$ to $R_7$ are all hydrogen.

74. A method according to claim 73 wherein $R_3$ is flourine at 4′ at the phenyl ring of substituent (II).

75. A method according to claim 65 wherein $R_3$ is fluorine, $R_4$ is lower alkyl, and $R_5$ to $R_7$ are all hydrogen.

76. A method according to claim 75 wherein $R_4$ is n-propyl.

77. A method according to claim 76 wherein $R_3$ is at position 4′ and $R_4$ is at position 2′ of the phenyl ring of substituent (II).

78. A method according to claim 68 wherein $R_3$ is lower alkanol, $R_4$ is hydroxy, $R_5$ is lower alkyl, $R_6$ and $R_7$ are hydrogen.

79. A method according to claim 78 wherein $R_3$ is at position 3′, $R_4$ is at position 4′ and $R_5$ is at position 2′ of the phenyl ring of substituent (II).

80. A method according to claim 79 wherein $R_3$ is acetyl and $R_5$ is n-propyl.

81. A method according to claim 65 wherein $R_1$ and $R_2$ and the one of $A_1$ and $A_2$ which is not a substituent of formula (II) are each hydrogen.

82. A method according to claim 81 wherein $R_3$ to $R_7$ are all hydrogen.

83. A method according to claim 65 wherein Q represents ethylene.

84. A method according to claim 65 wherein Q represents ethylene, propylene, butylene or pentylene.

85. A method according to claim 84 where one methylene group other than a methylene bound to an ether oxygen is substituted with hydroxyl.

86. A method according to claim 65 wherein Q is methylene or ethylene.

87. A method according to claim 65 wherein Q is propylene, butylene, pentylene or hexylene.

88. A method according to claim 87 wherein Q is propylene substituted by hydroxyl, butylene substituted by hydroxyl, pentylene substituted by hydroxyl or hexylene substituted by hydroxyl.

89. A method according to claim 88 wherein Q is 2-hydroxypropylene.

90. A method according to claim 65 wherein G is nitro.

91. A method according to claim 90 which comprises administering a compound selected from the group consisting of:

5-(2-[4-fluorophenyl]ethoxy)-2-nitroindan-1,3-dione
5-(3-[4-acetylphenyl]-propoxy)-2-nitroindan-1,3-dione.
2-nitro-5-(3-[2-n-propylphenyl]-butoxy)indan-1,3-dione, and the pharmaceutically acceptable salts thereof.

92. A method according to claim 65 wherein G is cyano.

93. A method according to claim 92 which comprises administering a compound selected from the group consisting of:

2-cyano-5-(2-phenylethoxy)indan-1,3-dione.
2-cyano-5-(2-phenylpropoxy)indan-1,3-dione.
2-cyano-5-(4-[4-acetyl-3-hydroxy-2-n-propylphenyl]-butoxy)indan-1,3-dione.

and the pharmaceutically acceptable salts thereof.

94. A method according to claim 93 which comprises administering a compound selected from the group consisting of:

2-cyano-5-(2-phenylethoxy)indan-1,3-dione, 2-cyano-5-(3-phenylpropoxy)indan-1,3-dione,
2-cyano-5-(4-[4-acetyl-3-hydroxy-2-n-propylphenyl]-butoxy)indan-1,3-dione, and the pharmaceutically acceptable salts thereof.

95. A method according to claim 65 wherein the administration is by insufflation.

96. A method according to claim 65 wherein administration is by injection.

97. A method according to claim 65 wherein administration is topical.

98. A method according to claim 65 wherein administration is oral.

* * * * *